(12) United States Patent
John

(10) Patent No.: US 11,266,839 B1
(45) Date of Patent: Mar. 8, 2022

(54) NEUROSTIMULATION USING PARTIAL SIGNAL COMBINATIONS

(71) Applicant: Michael Sasha John, Larchmont, NY (US)

(72) Inventor: Michael Sasha John, Larchmont, NY (US)

( * ) Notice: Subject to any disclaimer, the term of this patent is extended or adjusted under 35 U.S.C. 154(b) by 0 days.

(21) Appl. No.: 17/095,240

(22) Filed: Nov. 11, 2020

Related U.S. Application Data

(63) Continuation of application No. 16/778,240, filed on Jan. 31, 2020, now Pat. No. 10,864,376, which is a continuation of application No. 16/241,524, filed on Jan. 7, 2019, now Pat. No. 10,583,299, which is a continuation of application No. 14/334,371, filed on Jul. 17, 2014, now Pat. No. 10,188,864, which is a continuation of application No. 11/307,050, filed on Jan. 20, 2006, now Pat. No. 8,788,044.

(60) Provisional application No. 60/596,693, filed on Oct. 13, 2005, provisional application No. 60/594,321, filed on Mar. 29, 2005, provisional application No. 60/593,521, filed on Jan. 21, 2005.

(51) Int. Cl.
| | |
|---|---|
| *A61N 1/36* | (2006.01) |
| *A61N 1/372* | (2006.01) |
| *A61N 1/05* | (2006.01) |
| *A61M 5/142* | (2006.01) |
| *A61M 5/172* | (2006.01) |
| *A61N 1/04* | (2006.01) |

(52) U.S. Cl.
CPC ..... *A61N 1/36178* (2013.01); *A61N 1/36064* (2013.01); *A61N 1/36082* (2013.01); *A61N 1/37235* (2013.01); *A61M 5/14276* (2013.01); *A61M 5/172* (2013.01); *A61M 5/1723* (2013.01); *A61N 1/0456* (2013.01); *A61N 1/0529* (2013.01); *A61N 1/36071* (2013.01); *A61N 1/36114* (2013.01)

(58) Field of Classification Search
CPC ... A61N 1/0541; A61N 1/36038; A61N 1/375
See application file for complete search history.

(56) References Cited

U.S. PATENT DOCUMENTS

| | | | |
|---|---|---|---|
| 5,948,007 A * | 9/1999 | Starkebaum | A61N 1/36071 607/67 |
| 2004/0167584 A1* | 8/2004 | Carroll | A61N 1/0551 607/46 |
| 2006/0015153 A1* | 1/2006 | Gliner | A61N 1/36146 607/45 |

* cited by examiner

*Primary Examiner* — Amanda K Hulbert
(74) *Attorney, Agent, or Firm* — Rosenberg, Klein & Lee

(57) ABSTRACT

Stimulation treatments for various medical disorders, such as neurological disorders, comprise novel systems, strategies, and methods for providing TMS, electrical, magnetic, optical and other stimulation modalities. Some stimulation methods comprise varying the stimulation parameters to improve the therapeutic efficacy of stimulation, and decrease risk of habituation and side-effects such as interference with normal brain, sensory, motor, and cognitive processes. The creation, and subsequent variation, of stimulation parameters can use sensed data in order to match, adjust, or avoid matching characteristics of the stimulation therapy relative to certain endogenous brain activities. Novel methods are described for choosing, creating and subsequently stimulating with partial signals which summate to produce therapeutic vector fields having unique temporal patterns and low- or high-frequency spectral content. Improvements for the treatment of pain are disclosed.

17 Claims, 8 Drawing Sheets

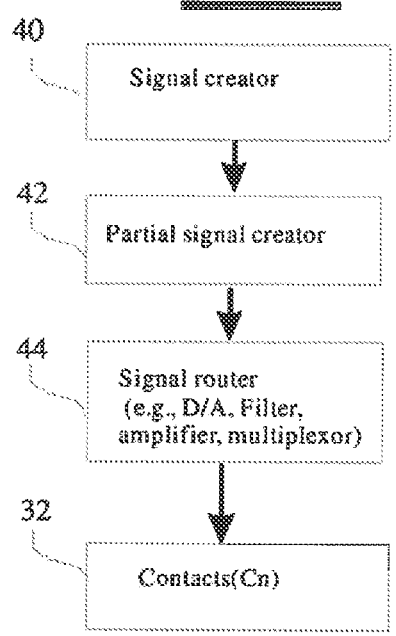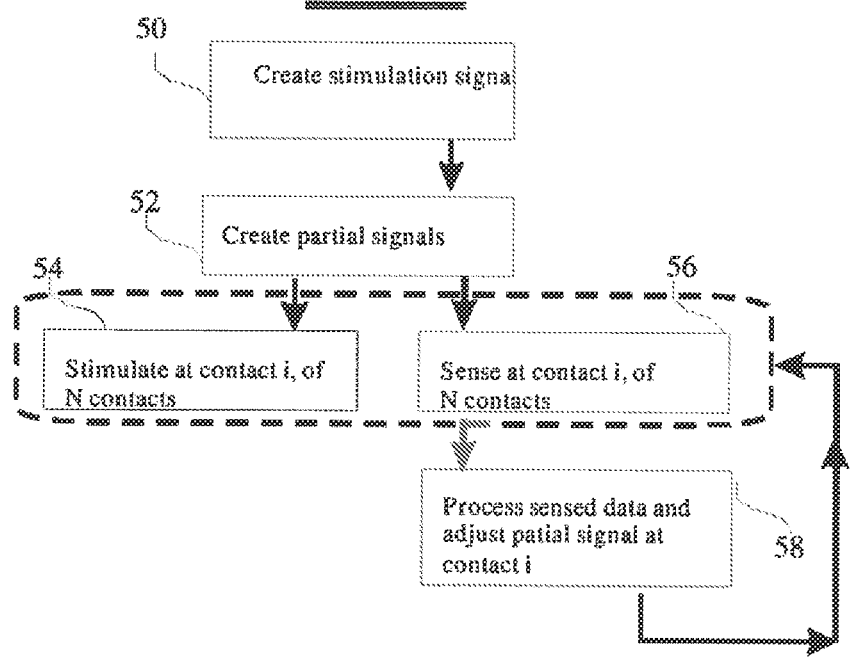

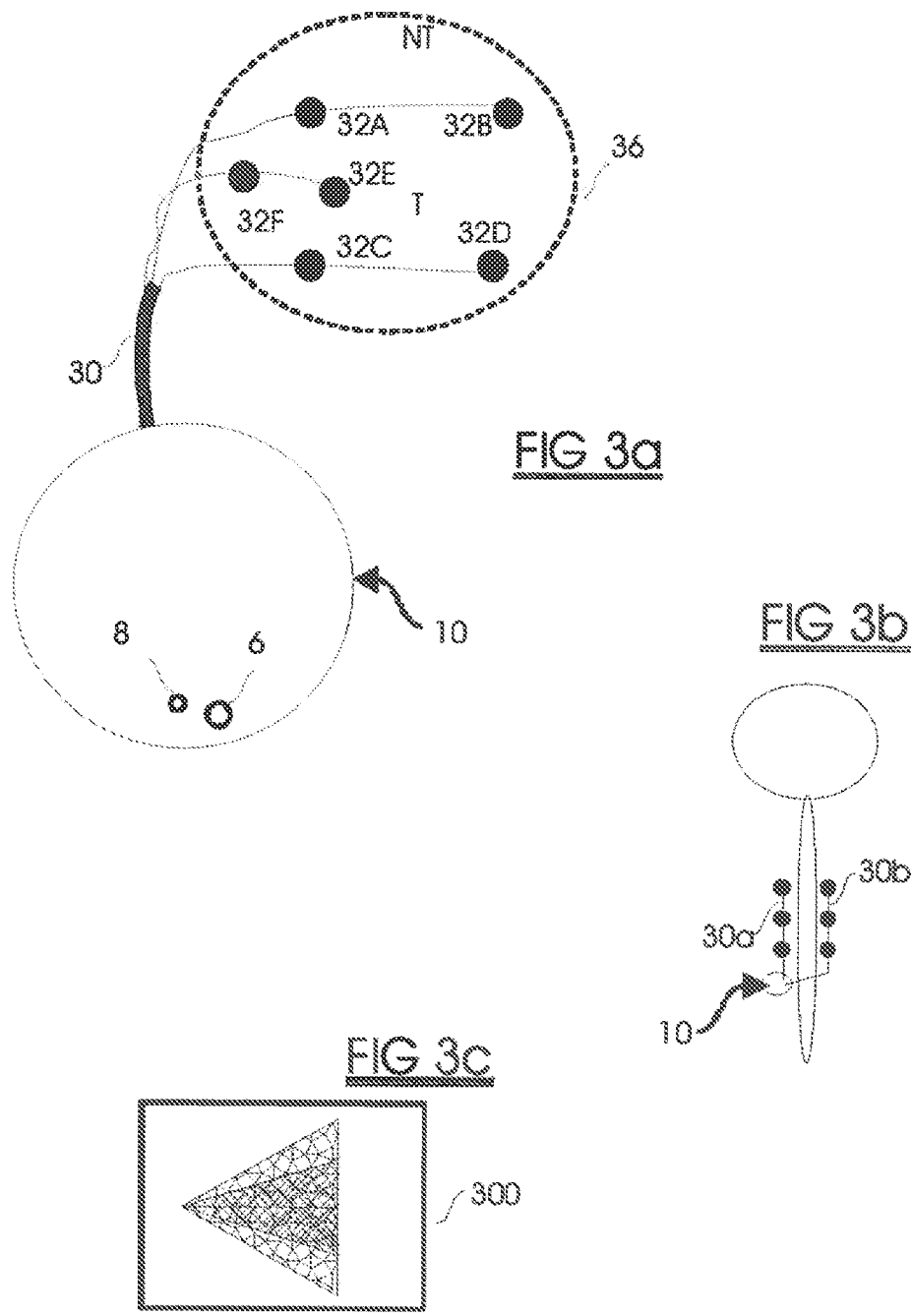

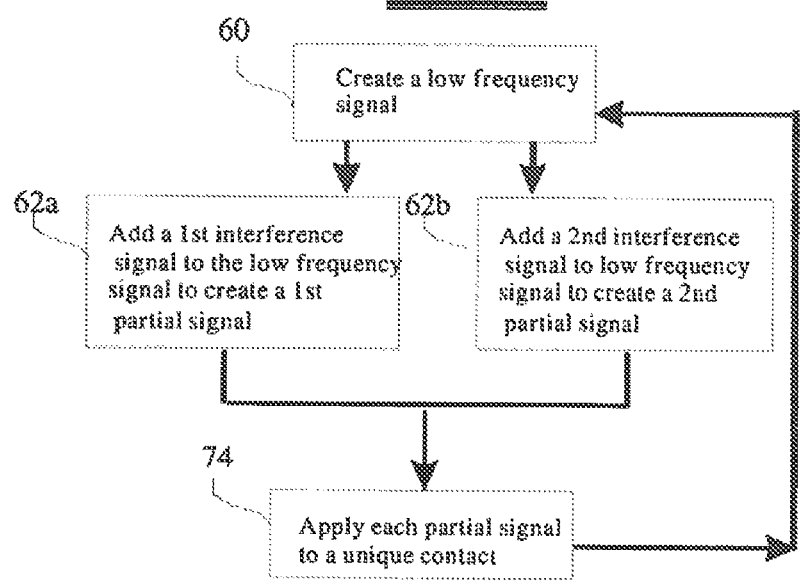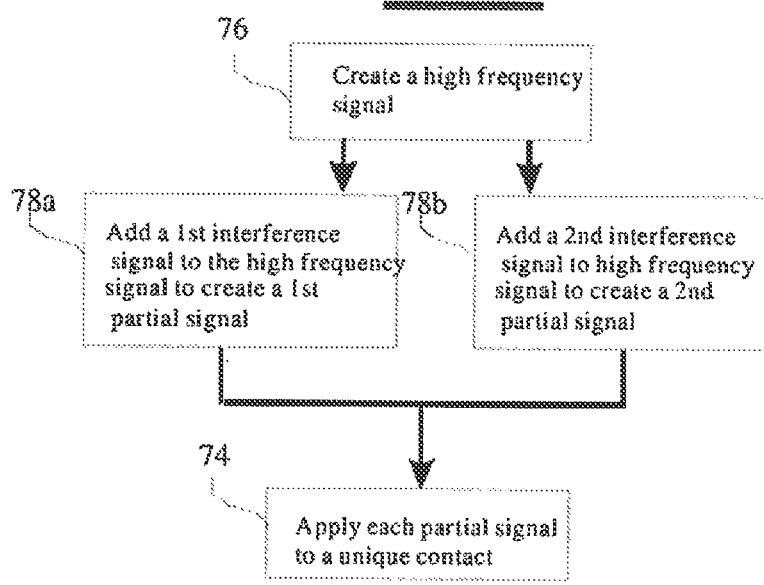

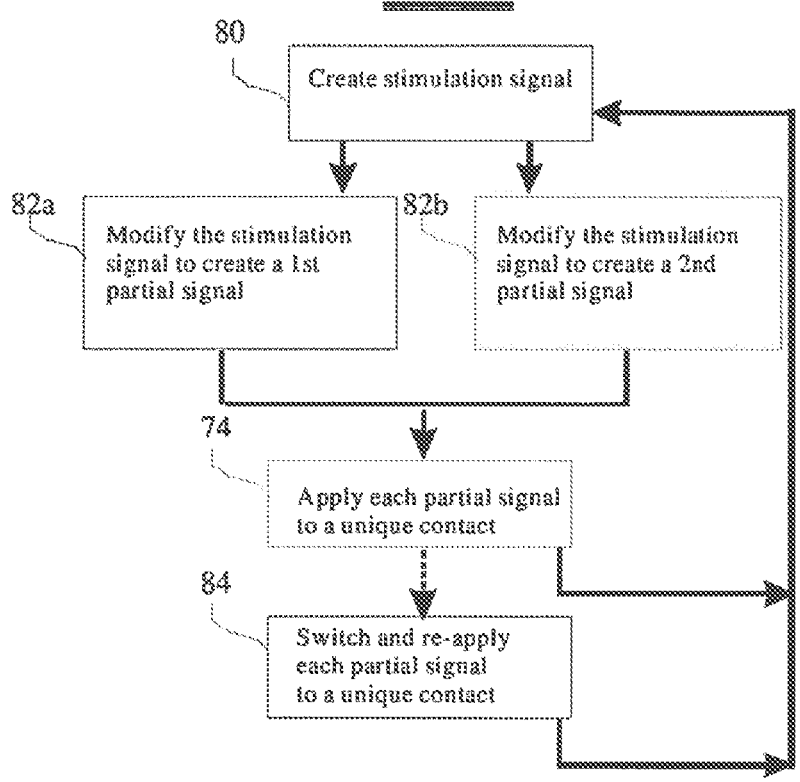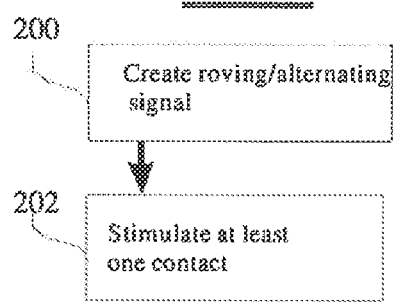

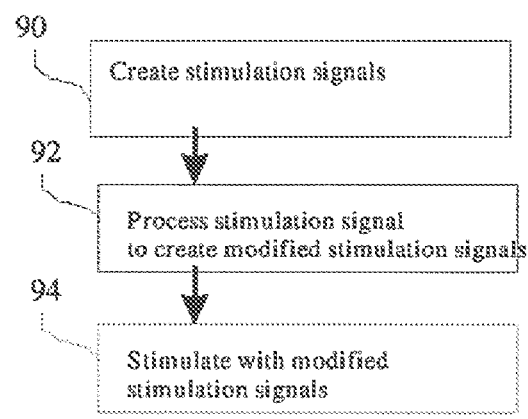
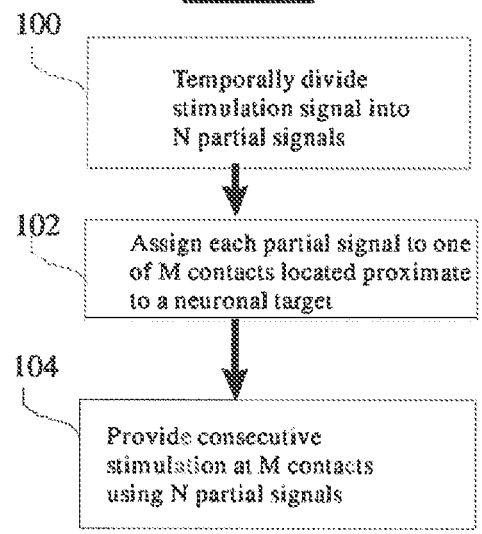

NEUROSTIMULATION USING PARTIAL SIGNAL COMBINATIONS

RELATED APPLICATIONS

This application is a continuation of U.S. application Ser. No. 16/778,240 filed Jan. 31, 2020, which is a continuation of U.S. application Ser. No. 16/241,524 filed Jan. 7, 2019, issued as U.S. Pat. No. 10,583,299 on Jul. 22, 2014, which is a continuation of U.S. application Ser. No. 14/334,371 filed Jul. 17, 2014, issued as U.S. Pat. No. 10,188,864 on Jan. 29, 2019, which is a continuation of U.S. application Ser. No. 11/307,050 filed Jan. 20, 2006, issued as U.S. Pat. No. 8,788,004 on Jul. 22, 2014, which claims priority of U.S. Provisional Application No. 60/593,521 filed Jan. 21, 2005, entitled "Systems and methods for treatment of epilepsy and other neurological and psychiatric disorders", and claims priority of U.S. Provisional Applications No. 60/594,321 filed on Mar. 29, 2005 and 60/596,693 filed on Oct. 13, 2005, both entitled "Systems and Methods for Tissue Stimulation in Medical Treatment", and incorporates these prior applications herein in their entirety.

FIELD OF THE INVENTION

The invention is directed to the treatment program used to guide stimulation treatments and includes providing novel stimulation signals used by implanted stimulators or external stimulation devices such as magnetic stimulators, which can induce currents in the brain or body of a patient, and which can be used in the treatment of medical disorders such as neurological, movement, and psychiatric disorders, or other disorders of the brain or body, and is particularly relevant to reducing the incidence of epileptic seizures.

BACKGROUND OF THE INVENTION

There are several problems which are encountered when providing stimulation, such as neurostimulation, in the treatment of a disorder. One problem is that the stimulation field is not optimally focused within a target area, and stimulation occurs in adjacent areas. For example, providing low frequency stimulation to one area may assist in treatment of some types of disorders such as epilepsy, while this same stimulation causes side-effects by unintentionally stimulating adjacent areas. If the target tissue is distal from the electrode, the intervening tissue will usually be stimulated with the stimulation pattern which is intended for the target area.

Providing certain types of stimulation to treatment areas, while supplying different types of stimulation to non-target areas, can decrease the occurrence of side-effects and enable improved treatment. Other problems which arise when electrically stimulating tissue are related to the transfer of energy from the electrical contact to the immediately adjacent tissue as well as through tissue itself. While certain types of stimulus waveforms may be good for treatment, these may be less well suited for transmitting energy from the electrodes to tissue, and subsequently through tissue itself. One approach to optimizing the desired effects of stimulation is to construct a "carrier wave" comprised of an oscillating carrier such as a train of high frequency pulses at some high frequency, f(H), which is modulated by some lower frequency mf(L) or contour mc(L). The contour itself may be an arbitrary waveform, a sine wave, an envelope derived from sensed activity, or a ramp of a specified rate of change of amplitude. This approach may be improved by changing the carrier frequency f(H) or by changing the modulating contour or its frequency at specified or random intervals, in order to increase entrainment and avoid habituation or adaptation to the stimulation. Another solution is to use signals which have desired characteristics for stimulation of, or transmission through, tissue which is not the target tissue, and which combine to create a vector field which stimulates target tissue in a desired manner. While methods of combining stimulation signals to produce desired vector fields have been used for dermal stimulation, and stimulation of other tissue, the methods described here are novel from, and offer advantages over, those of the prior art.

PRIOR ART

The methods and systems of the current invention are novel from and advantageous over prior art that has addressed the some of the issues described above. For example, US 20030135248 entitled 'Variation of neural-stimulation parameters' (the '248 application) describes improving therapy, and minimizing energy consumption, side-effects, and tolerance by pseudo-randomly varying at least one parameter and simultaneously varying a second parameter based upon a predetermined relationship specifying how the changes in one parameter affect the values for the second parameter with respect to neural excitation (e.g., with respect to the strength-duration relationship). The idea here is that it may not be possible to achieve the desired therapeutic effect without unwanted side-effects of stimulation when a large volume of tissue is simultaneously modulated. By pseudo-randomly varying the spatial pattern of the modulated neural structures, it may be possible to minimize undesired side-effects such as adaptation to the stimulation signal while still attaining the desired therapeutic efficacy. Although this prior art varies stimulation at one electrode based upon stimulation at another, it does not discuss a method of diminishing side-effects by providing subthreshold stimulation (e.g., due to spectral content) at multiple leads which are physically configured so that the energy combines to the extent needed for clinical efficacy (e.g., as an interference pattern, a harmonic or a sub-harmonic, or otherwise produces effective stimulation frequencies) primarily in the area where neurostimulation is desired, which is part of the claimed invention.

The methods and systems of the current invention are also novel from and advantageous over prior art that has addressed the issues of fixed electrode placement. For example, US 20020022866 entitled 'Multichannel Stimulator Electronics and Methods' and U.S. Pat. No. 6,662,053 (both to Borkan) describe improving therapy by providing a system for virtually "repositioning" electrodes by changing the strength and other stimulation parameters in order to reshape the electrode field. This non-invasive repositioning may be advantages in cases of post-surgical electrode-migration, when surgical placement fails to produce results, and to "accommodate" endogenous alterations which may cause the exact target location to change over time. Similarly in U.S. Pat. No. 6,393,325 (to Mann et al) "Directional programming for implantable electrode arrays" is described in which the position of the stimulation field is virtually readjusted after surgery by programming the array to deliver stimulation at different locations in the tissue. In US 20030078633 (to Firlik et al.), systems and methods for providing transcutaneous and subcutaneous stimulation are provided which rely upon multiple electrode locations in order to provide stimulation fields of different shapes and strengths, mostly oriented towards spinal stimulation, although these can be used for other types of stimulation as well. The Borkan, Firlik, and Mann inventions are designed to non-invasively alter the size, shape, orientation, and position of the vector field. These do not describe using temporal and spectral signals which produce different stimulation effects in the vector field than those which are produced in non-target areas, which is a primary advantage offered herein. Further, the prior art doesn't describe or anticipate using spectral and temporal characteristics of the vector field to decrease side-effects, and tolerance by pseudo-randomly varying at least one parameter, which is part of the present invention. The methods and systems of the current invention are novel from and advantageous over other prior art as well, as is partially illustrated in the following objects of the invention. There is disclosed an object of providing a unique stimulation signal to a neural target relative to adjacent areas. In one embodiment two or more stimulation leads are used, which are located proximal enough to permit the summation of a vector field having spectral content that stimulates a desired area to provide therapeutic benefit, while not imposing this type of stimulation in adjacent areas. Accordingly, the fields outside the target area stimulate the non-target areas in a differential manner or do not stimulate these areas. There is also disclosed using two or more stimulation leads which stimulate at subthreshold levels (e.g., using ineffective waveshapes), in order to reduce the amount of side-effects (which occur in non-target tissue), but which are positioned and oriented to cause their fields to combine effectively to produce therapy in target tissue.

These and other features of the claimed invention will expanded upon in the following material which describes numerous preferred embodiments of the systems and methods. It is obvious that the exact details for accomplishing the embodiments described herein can be modified without departing from the spirit of the inventions.

SUMMARY OF THE INVENTION

Illustrative embodiments of the invention are provided, which overcome the above noted, and other, deficiencies of alternative methods and systems of stimulation, such as those currently relied upon by multiple-lead stimulators. The illustrative embodiments provide techniques for improving stimulation, which may be deep brain stimulation, to treat various disorders, by decreasing the risk of: using incorrect stimulation parameters; stimulating non-target tissue; development of tolerance; and other unwanted effects. While neurostimulation, especially with respect to treatment of seizures, is emphasized in some of the material here, the treatment of other disorders of the brain and body are also described and are no less central to many of the advantages of the inventive principles. Accordingly, the stimulation techniques described here can be applied to the brain, the spinal cord, cranial and vagus nerves, or other area of the body, during modulation for the treatment of disorders, such as epilepsy, psychiatric conditions, migraines, headaches, pain, tremor, and depression, traumatic brain injury, cerebovascular accidents, strokes, thrombosis or aneurysm, or used for the treatment of disorders such as cardiac disorders which can be treated via CNS targets or by direct stimulation of cardiac tissue. Stimulation can also be applied for treatment of wounds, infection, degenerative disorders, injury, healing acceleration, bone growth, and promotion and direction of certain types of cell growth and metabolic activity. The systems and methods of the invention can also be applied to the vagus and other nerves related to modulation of the central and peripheral systems (e.g. unilateral or bilateral stimulation of the trigeminal nerves), and can also be applied to stimulation of other areas of the body such as the cardiovascular system, digestive system, skin, muscle, spine, nerves related to pain, or other tissues or organs. Further, sensed data related to any of these disorders can be sensed from both the brain and/or body. Sensing and stimulation can occur in regions of the brain and body which are the same or different.

In one embodiment, a treatment parameter is systematically varied, and sensed data are collected and processed, in order to determine what values successful led to desired treatment effects. These successful parameters can then be selected and relied upon for during treatment.

In another embodiment two or more electrode leads each stimulate using partial stimulation signals of different spectral compositions. For example, the stimulation signal to be used at each electrical contact can be added to an interference signal, so that the vector summed signal in the tissue approximates the stimulation signal (e.g., FIGS. 5a, 5b). Alternatively, each lead can use a stimulation signal having stimulation frequencies which are separated by a frequency which is a beat frequency, which, for example, may be maintained within a specific therapeutic frequency range over time (e.g., between 4 and 8 Hz). Further, the instantaneous frequencies of two signals can be varied considerably while maintaining a constant beat frequency, for example, in order to decrease tolerance or increase entrainment to the stimulation or to avoid certain side effects in the non-target tissue. In a preferred embodiment of the present invention to utilize beat stimuli which are created from stimulation at two or more electrode contacts, the stimuli being modulated at least at two different rates which differ between at least approximately 0.5 Hz and at most by approximately 20 Hz.

The invention uses vector field signals which are determined to be clinically effective. The sets of partial frequencies which create the therapeutic vector signals when provided at specific electrodes (with consideration to electrode geometry when appropriate) can be chosen and tested automatically, or by a physician or patient. Sets of partial frequencies which provide therapeutic stimulation while not producing unwanted side-effects can be stored in a database and selected for treatment. These sets can then be chosen and utilized according to sensed data, according to time information, according to patient request, or by other methods.

The use of partial stimulation signals can be beneficial because only the target tissue (e.g., neuroanatomical area) which is commonly influenced by the stimulation signal of two or more electrode leads will be stimulated with the vector signal while other areas, within which stimulation may not be necessary, are not stimulated by the vector signal. Accordingly, the target site can be stimulated with a low frequency while adjacent non-target sites are stimulated using a significantly different frequency range. In other words, the target-signal and non-target signal generally have different spectral, spatial, and temporal characteristics, which can cause, or not cause, modulation of tissue or which can selectively modulate certain cell types. In one embodiment of this method, two or more stimulating electrodes are positioned so that their combined fields can superimpose at, or near, the areas of epileptic foci. By increasing the strength of the stimulation at a subset of the electrodes, with consideration of electrode geometry, the spectral content and area of maximum superposition can be adjusted. The adjustment of the spectral and temporal content of the stimulation signals and the vector field, and the shape of these fields can be assisted by an external patient programmer, which has graphical displays of the field properties that enable a user to custom tailor the treatment for a patient, and which communicates with one or more stimulation devices providing the therapy.

Some stimulation methods comprise varying the stimulation parameters to improve the therapeutic efficacy of stimulation, and decrease risk of habituation and side-effects such as interference with normal brain, sensory, motor, and cognitive processes.

Other advantages, novel features, and further scope of applicability of the invention will be described in the following illustrations and description.

BRIEF DESCRIPTION OF THE DRAWINGS

For the purpose of illustrating the invention and its advantages, there is provided a detailed description and accompanying drawings of embodiments which are presently preferred. In illustrations of the methods, when arrows indicate iteration (a return from later steps to prior steps), this iteration is understood to be a preferred embodiment, and executing the steps a single time may also be an option. In the illustration of methods, steps which occur sequentially may also occur concurrently, in parallel, or may be repeated several times (e.g., in order to obtain an estimation of a measure by computing a statistic such as the mean), prior to the next step occurring. It is understood that the invention is not intended to be limited to the precise arrangements and instruments shown, wherein:

FIG. 2a shows a schematic block diagram representation of a system designed to create partial signals to be used during neurostimulation, this can be implemented in the stimulation sub system;

FIG. 2b shows a schematic block diagram representation of method of using a system designed to create partial signals to be used during neurostimulation;

FIG. 3a illustrates an embodiment of an implantable stimulation system including a device having 6 electrodes that are implanted in the neural tissue of a patent;

FIG. 3b illustrates an embodiment of an implantable stimulation system including a device having 2 stimulation arrays located bilaterally to a patient's spine;

FIG. 3c illustrates an embodiment of a display screen which is part of an external patient programmer which displays the shape, location, orientation, strength, spectral, and other characteristics of two or more stimulation fields of the partial signals and the vector field;

FIG. 5a shows a schematic representation of the operational flow of a method designed in accordance with a preferred embodiment of the present invention, wherein two partial signals are created by adding interference signals to a low frequency base signal;

FIG. 5b shows a schematic representation of an alternative method designed in accordance with a preferred embodiment of the present invention, wherein two partial signals are created by adding interference signals to a high frequency base signal;

FIG. 6 shows a schematic representation of an alternative method designed in accordance with a preferred embodiment of the present invention, wherein two partial signals are created by splitting, or otherwise deconstructing, a base stimulation signal, and wherein these partial signals are subsequently re-assigned to different contacts at different moments in time;

FIG. 7 shows a schematic representation of another method designed in accordance with a preferred embodiment of the present invention, wherein a parameter of the stimulation signal, such as the frequency of a signal is roved, or alternated, between at least two frequencies, during the therapy;

FIG. 8 shows a schematic representation of an alternative method designed in accordance with a preferred embodiment of the present invention, in which rather than relying upon the creation of new stimulation signals, stimulation signals are modified before being applied in order to alter the stimulation signals at different moments in time;

FIG. 9 shows a schematic representation of another method designed in accordance with the present invention, wherein the stimulation signal is temporally distributed across a number of stimulation locations; and, FIG. 10 shows a device for providing responsive and/or non-responsive transcranial magnetic stimulation to a patient.

DETAILED DESCRIPTION OF THE PREFERRED EMBODIMENTS

Figure 1A:
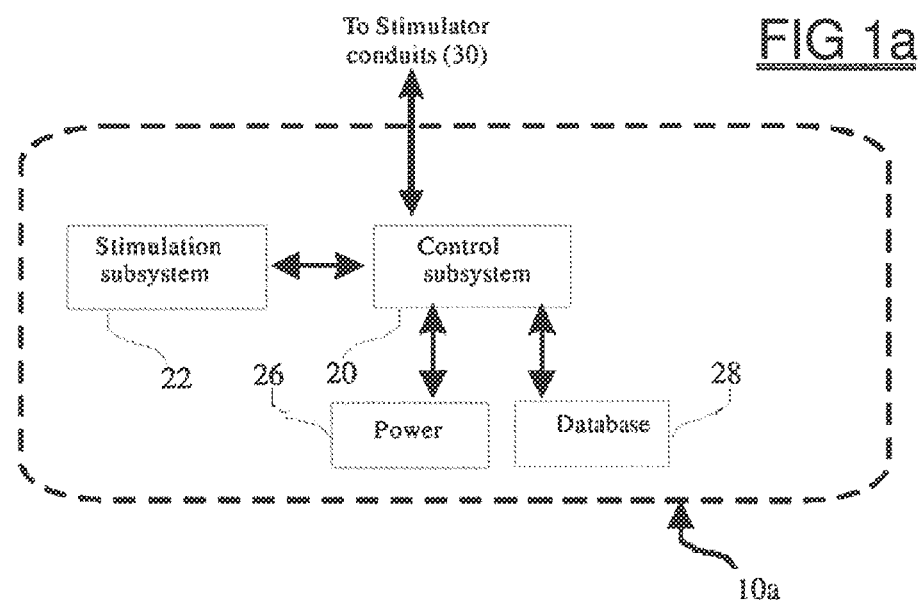
FIG. 1a shows a schematic representation of one embodiment of a neurostimulation system which can be used in the current invention.

This specification describes improved systems and methods for stimulation of tissue, which may include deep brain neurostimulation. The following material provides a general understanding of terms used in this specification, with the understanding that these terms can be further adjusted or modified or altered within the specification itself to achieve different specific embodiments of the invention.

As used herein the terms "stimulation system" or "stimulator" refers to a device comprised of components which are either configured in a distributed manner or are primarily contained within the housing of device such as an implantable device, and which can modulate tissue by delivering one or more of electrical, optical, magnetic, or drug therapy. The stimulator can be a generic implantable stimulator such as those manufactured by Medtronic, NeuroPace, Cyberonics, NeuroBionics, and Advanced Neuromodulation Systems, which can be configured or adapted to provide electrical stimulation according to protocol that may be fixed or which may be adjusted based upon a clock signal and/or state of a patient. In some embodiments, the stimulator can also include a generic drug pump, such as those manufactured by Medtronic, Johnson & Johnson, or Advanced Neuromodulation Systems, which can be configured or adapted to provide drug stimulation according to a fixed protocol, or in response to a clock signal or sensed data. Accordingly, the stimulator 10, can be realized, for example, using either electrical signal generating stimulators 10 a, or a combination of the two 10 b. The stimulator can also take the form of a transcranial magnetic stimulator, sonic, or other stimulation device, with components located partially or completely outside of the patient.

As used herein the term "stimulation conduit" can include one or more electrical leads, each having at least one electrical contact. The stimulation conduit can also be one or more electrical contacts of a lead. The stimulation conduit can also be one or more catheters, each of which can be a simple catheter or a combination catheter/lead also capable of providing electrical stimulation or sensing in conjunction with drug delivery. The stimulation conduit can also include an optical fiber or transducer, including infrared generating devices, or may be realized as an electromagnetic coil, and can include sound transducers including those related to the providing ultrasound treatment. Stimulation conduits can be configured to be configured to be positioned in, on, near, or otherwise adjacent to tissue, such as nerve tissue and neurons, and can include a number of embodiments including plate electrodes, percutaneous leads (e.g. a tripole percutaneous lead), circumferential leads, laminotomy, paddle, and bifurcated stimulation leads, cuff leads, and directional electrodes.

As used herein, the term "sensor" can refer to a device for measuring an electrical, chemical, optical, or other physical property of the patient. A sensor may provide sensed data relating to multiple measures, for example, the flow rate, concentration, and pressure of a fluid. Accordingly, a sensor may be an aggregate of several types of specialized structures each configured to sense a different characteristic of the environment in which it is located. The sensors can also include electrochemical sensors (e.g., microelectrode arrays made by Quanteon for measuring substances such as glutamate), or optical sensors (e.g., which can detect $O_2$, $CO_2$, and PH levels, and which can take the form of pulse oximeters or chromophore-based IO biosensors having one or more sensing fibers), and can detect physical measures (e.g., pressure, temperature, flow, acceleration), enzymatic changes, or the state of tissue or an organ. The sensor can be an electrical contact that may also provide stimulation at times which sensing does not occur at the contact. The sensors can be biosensors which are capable of sensing one or more specific molecules or other biological substances, either directly or by means of their metabolites. The sensors can also be biosensors, or equivalents such as a chemically sensitive/enzyme sensitive field effect transistor, capable of sensing neurochemicals such as neurotransmitters. U.S. Pat. No. 5,791,344 to Schulman et al. entitled "Patient Monitoring System," proposes a system to monitor the concentration of a substance in a subject's blood wherein one enzymatic sensor is inserted into a patient to monitor glucose. Similarly, EP1011797 to Schulman et al, entitled "System of Implantable Devices for Monitoring or Affecting Body Parameters," proposes using microsensors to measure, for example, glucose level, oxygen content, temperature, and other measures. A sensor may sense, for example, EEG, neurotransmitter levels, cardiovascular measures such as heart or respiration rate, glucose level, oxygen saturation level and other types of information in order to measure state of the subject.

When possible, the invention can rely upon completely implanted sensors, but may also communicate with, external devices, or may utilize information derived from assays, or laboratory techniques, in order to obtain accurate sensed data of the desired measures. In the case disorders such as a movement disorder, a sensor may be a motion detector, microphone, or EMG sensor implanted, for example, in a limb (the data of which can be filtered and processed in order to also measure the patient's EKG and its related measures such as interbeat-interval), or can be an EEG sensor located, for example, over somatosensory/motor areas of the brain.

The sensor can communicate with and obtain power from the stimulator 10 or can have its own power source and communicate via telemetry, or by optical or sonic signal, and can also be a device external to the patient which communicates with the patient programmer or stimulator 10. Alternatively, one or more sensors can communicate with the stimulator for example, the control subsystem 20 using a port/bus, with address, data, control lines and other hardware required for successful communication. Analog-to-digital conversation, and conversion of raw data to meaningful units (e.g., signal processing, such as measuring the power in a limited frequency band after time-to-frequency conversion of the data, can reflect the size of a tremor) can occur at the level of the sensor or can occur in the stimulator 10.

As used herein "treatment program" determines the parameters for the stimulation, sensing, and evaluation protocols, or determines, if, how, why, and when the protocols are altered. The treatment program can be implemented in hardware (e.g., a control circuit) or software form and can be implemented by the control subsystem 20 for providing treatment. The term "treatment" can simply mean decreasing or deterring one or more unwanted symptoms of a disorder or creating an advantage which would not occur if treatment wasn't provided. The treatment program can utilize treatment parameters and protocols in order to modify any method of the treatment, including modification and control of operations and protocols which perform sensing, evaluating sensed data, or stimulating.

As used herein "stimulation subsystem" provides stimulation, via at least one stimulation conduit, according to the parameters of a stimulation protocol which determine where, when, and how to stimulate with, for example, one or more of electrical, optical, or other stimulation. Not only the type of stimulation but also the number and location of sites at which stimulation can occur are defined by the stimulation protocols. The stimulation protocol can be selected or adjusted based upon time information, sensed data, the state of the patient, or a combination. A stimulation parameter can determine each of the characteristics of a stimulation protocol, such as level of stimulation (e.g., voltage or current), occurrence of stimulation (e.g., duration, duration per unit of time), type and site of drug delivery, signal characteristics such as signal shape and many other characteristics as is known in the art. A stimulus parameter can be a spectral parameter, which relates to the amplitude, phase, and frequency of at least one component of the stimulation signal. A stimulus parameter can also be a pulse parameter, such as pulse frequency, amplitude, width or shape. The overall shape of the stimulation signal can also be sinusoidal, arbitrary, or can approximate different trigonometric functions.

As used herein the term "sensing subsystem" refers to a subsystem which provides sensing according to the parameters of a sensing protocol which determines where, when, and how to sense with one or more sensors which may detect, for example, electrical, optical, or chemical information. The sensing subsystem may have a detection subsystem module which is configured to detect and or measure specified events, or states, and can include programmable signal conditional circuitry and algorithms. The sensing protocol can be selected, or adjusted, based upon, for instance, time information or the state of the patient or both As used herein the term "control subsystem" refers to a subsystem which provides control of the treatment and can implement a treatment program. If sensed data are obtained by the stimulator, the control subsystem can rely upon an evaluation protocol to determine if, when and how to evaluate the sensed data and determines if stimulation occurs in response to the sensed data. The evaluation protocol can be selected or adjusted based upon time information or the state of the patient, or both. The control subsystem can also use a control circuit to implement control laws based upon measures of sensed data, provided by the sensing subsystem, in order to enact therapy.

As used herein the term "treatment criterion" usually refers to a criterion to which sensed data are evaluated or compared using the evaluation protocol. The results of this comparison can determine what type of stimulation takes place. For example, failure to meet a treatment criterion may cause stimulation to occur or may cause a change in a protocol parameter, or may cause a different stimulation protocol to be selected. Alternatively, success in meeting a treatment criterion may cause stimulation to be halted or may cause the same stimulation protocol to be selected again. It is obvious that the logic of treatment criterion can be inverted, and several criteria can be combined sequentially or in parallel in order to provide therapy without departing from the spirit of the invention illustrated and described in the embodiments of this description of the invention.

As used herein, "basal signal" or "basal stimulation" refers to the application of stimulation intended either to decrease the probability of an adverse event occurring, such as a seizure, or to modulate activity related to a disorder such as psychiatric illness or tremor. The basal signal is generally applied non-responsively, continuously, or periodically applied, although it can be adjusted or selected based upon the treatment program, time information, or sensed data.

As used herein, "base signal" normally refers to a signal which will be modified or used to determine two or more partial signals. The partial signals will normally combine to form a "vector sum field", in the tissue of the subject which approximates the base signal.

As used herein, "responsive" stimulation refers to the application of stimulation which occurs in response to evaluation of sensed data, such as the detection of a medical event, state, or activity related to a symptom of the disorder.

As used herein, the terms "event", "detection of event" or "medical event" refer to the sensing of data and the analysis of this data which confirms that abnormal or unwanted activity, such as a seizure, tremor, or other activity related to a disorder was detected, or indicates that or at least one biochemical index has assumed a value that is above or below a specified criterion.

As used herein, "seizure" refers to behavioral or electrophysiological signature of an impending or existent seizure, and includes epileptiform activity.

As used herein, "amplitude" may refer to either voltage or current of a stimulation signal (while the other is held constant or also varied), and may be scaled or adjusted based upon impedance characteristics and/or electrode geometry.

FIG. 1a is a schematic of the components of a preferred embodiment of the stimulator 10 a and includes a control subsystem 20 a stimulation subsystem 22, a power source 26, such as a rechargeable battery, and a memory storage structure such as a database 28. The control subsystem 20 contains electronics which are commonly incorporated into implanted devices such as specialized circuits for carrying out the tasks involved in providing stimulation therapy (e.g., see U.S. Pat. No. 6,066,163, US20020072770, and US20050240242). Accordingly, the control subsystem 20 can contain telemetry circuits, programmable memory, a microprocessor, a timer/clock, multiplexors, switches/relays and other components which are used currently within implantable stimulators as is known to those skilled in the art. Similarly, the stimulation subsystem 22 can include hardware needed to provide transduction of different pulses and other waveshapes, and transduction means for providing electrical, optical, magnetic or other type of stimulation. The stimulation subsystem 22 can include programmable signal generators, amplifiers, filters, DSP modules, regulating circuitry for voltage, current, impedance (e.g., impedance sensing and matching circuitry for both high and low impedance states associated with different signals and endogenous conditions and variable impedance networks), polarity and charge-balancing operations. The stimulation subsystem 22 can program the conduits to stimulate in a bipolar, monopolar, or in both modes, containing one or more polarity switches. The stimulation subsystem can provide independent amplitude and stimulation control for each of all the stimulation conduits and can include interelectrode sensing and calibration circuitry and routines for adjusting the partial signals to produce the intended vector field in the intended location as well as circuitry for changing the size, shape, position, spectral and temporal characteristics of the vector field.

In order to create stimulation signals a programmable frequency generator can be used by the stimulation subsystem 22 which sends a signal to a pulse-width control module for creating pulses which are sent to a digital-to-analog converter and an amplifier for amplifying the signal that is to be used during treatment. Additionally, pulse width/amplitude circuits can be used. The stimulation subsystem 22 can also include hardware and/or software for providing the treatments described in this application, including, for example, partial signals such as can be generated using methods and systems shown in FIG. 2 a and FIG. 5 b. A clock can be included in the control subsystem 20 to provide time information in order to permit the control subsystem 20 to select or adjust stimulation protocols based upon time information. The protocols can be stored in the memory, which is realized here as a querieable database 28, which permits the control subsystem 20 to obtain information such as stimulation parameters for various stimulation protocols, self-norm data, and other information relevant to providing therapy. At various times prior to, during, or after implantation, the control subsystem 20 can be programmed to select or adjust protocols in relation to predetermined counts of the clock, durations (e.g., time since the last stimulation protocol was selected), or times of day. The patient may adjust the therapy program of the control subsystem 20 to provide stimulation via the stimulation subsystem 22 using stimulation protocols that are selected or adjusted. The control subsystem may also be supplied with memory for computational needs. The stimulation subsystem 22 can be controlled by an external patient programmer which allows the patient to select different stimulation protocols, different stimulation waveforms and different sets of partial signals and their associated montages and characteristics. Using a graphical user interface of the external programmer, a medical professional can direct the stimulation subsystem 22 with respect to the characteristics of the stimulation protocol to use at any particular electrode and also to shape or move the virtual vector field in a particular fashion. The calibration method displayed in FIG. 2b can be used in order to calibrate or confirm the model used by the subsystem 22 or external patient programmer.

Although shown as separate components for purposes of illustration, the components of FIG. 1a and many of the other FIGS. provided herein can generally be realized on a single circuit board, and can even be realized as a microchip which contains specialized circuitry for amplification, DA/AD conversion, digital and analog signal processing, memory, timing, clock, and communication circuitry which are powered by a power source. When the stimulator provides drug therapy, the electronics of the stimulation subsystem 22 can supply control of, and power to, one or more pumps for dispensing one or more drugs, stored in a reservoir assembly, according to the stimulation protocol.

Figure 1B:
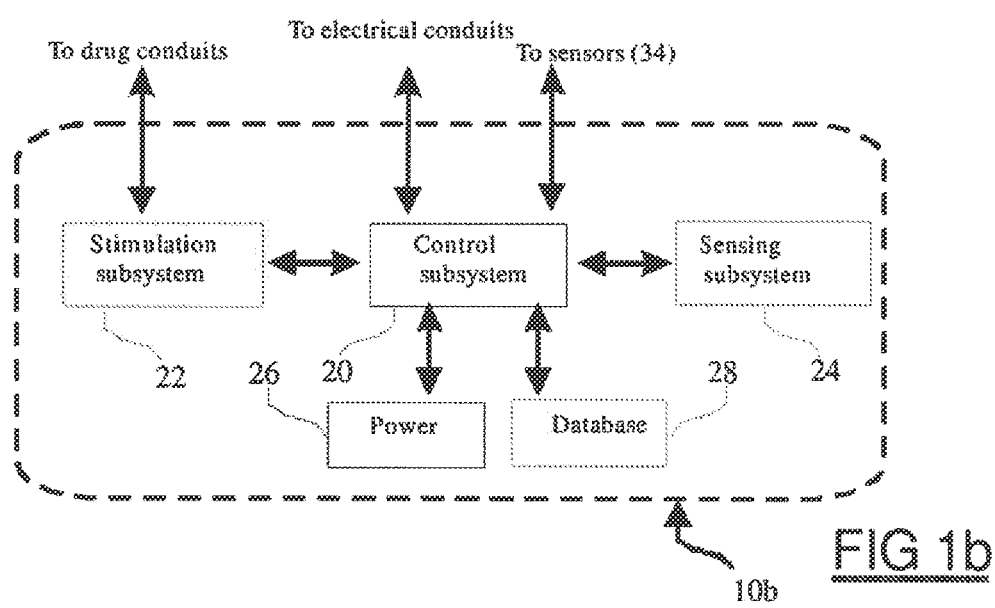
FIG. 1b shows a schematic representation of an alternative embodiment of a neurostimulation system which can be used in the current invention, which provides drug stimulation, in addition to other types of stimulation.

FIG. 1*b* is a schematic of another preferred embodiment of the stimulator 10 *b* and includes a control subsystem 20, a stimulation subsystem 22, a sensing subsystem 24, a power source 26, and a database 28. The sensing subsystem 24 can provide analog-to-digital conversion circuitry, memory, multiplexing circuits, relays, signal processing circuitry, or other circuitry which is not provided in the control subsystem and which is needed to obtain, analyze, amplify, process, and store the sensed data obtained from at least one sensor. The sensing subsystem 24 can perform processing of the sensed data, such as amplification, signal processing, filtering, spectral analysis, time-frequency analysis, state-analysis, modeling, comparison operations which can be statistically based and utilize logic operations, and can provide for temporal analysis and pattern matching as may be used to detect epileptiform, tremor, or other activity related to the disorder being treated. The sensing subsystem 24 senses data according to the parameters of a sensing protocol. A stimulator conduit, such as 30 of FIG. 3, can be realized as leads, each of which serve both as a stimulating electrode and also as a sensor. Each contact 32 *a*-32 *f* can serve both as a sensor, when the contact 32 functionally communicates with the sensing subsystem 24, and as a stimulator, when the contact 32 communicates with the stimulating subsystem 22. The physical connection between the contact 32 and either the sensing 24 or stimulating 22 subsystems can be controlled by a micro-relay or switch, such as a make-before-break double-throw relay which can be located in the control subsystem 20. Alternatively, sensors 34 and contacts 32 may be physically distinct, for example, as in the case where the sensors 34 measure optical, chemical, pressure, temperature, movement, or other physical aspect of the region from which the sensed data are obtained. The electrical stimulation/sensing can be mediated directly by the control subsystem 20, or can be accomplished by means of the stimulation and sensing subsystems 22, 24, which are under control of the control subsystem 20, as is the case for drug delivery FIG. 1*b*. When stimulation includes the delivery of drugs, then these can be dispensed through the drug conduits of the stimulation subsystem 22.

When used to treat seizures, at least one sensor 34 can be situated in a brain region, such as an epileptogenic lesion, an epileptogenic region, a spike focus, a focal functional deficit, an irritative zone, a structure of the limbic system, or the temporal lobe, or any structure which is characterized by abnormal electrical or neurochemical activity. Alternatively, when used to treat pain one sensor 34 can be in the brain, spine, or peripheral nerves to detect activity related to pain, and the stimulation electrodes can be located to stimulate target areas of the vagus nerve. Further when used to promote chemotherapy a drug sensor 34 can be in a region near a tumor, and the stimulation electrodes (or external magnetic stimulator coils) can be located to modulate electroporation, or activation of a nano-particle containing drug, which is approximately localized to the tumor target by the spectral, temporal, or other characteristics of the vector field. Generally, by using multiple electrodes to stimulate a given area these may each stimulate in a subthreshold manner, while the energy in the anatomical area that is commonly stimulated by the different electrodes, can summate and produce a signal with characteristics (e.g., spectral characteristics, pulse shapes, and current/voltage strength) which can modulate the target tissue to provide the intended therapy either alone, or in conjunction with other therapies.

FIG. 2A shows a schematic representation of a system designed to create partial signals which are used during stimulation. This system can be incorporated into the stimulation subsystem 22. A signal creator 40 works with a partial signal creator 42 in order to create the partial signals. In one method the signal creator 40 supplies a base signal to a partial signal creator 42, which then modifies the signal to create a number of partial signals. For example, by adding selected interference signals to the base signal, partial signals can be created so that their summation leads to a vector field which is approximately the base signal. The size and polarity of the interference and partial signals can be adjusted, by the partial signal creator, based upon an algorithm which incorporates the spatial location and orientation of the electrode contacts (or optical outputs). In an alternative method, the signal creator 40 controls the partial signal creator 42 and directs it to provide the partial signals according to a specified algorithm. In one instance, where the intended vector signal is a beat at a particular frequency, the algorithm can choose 2 partial signals that are separated by a specified frequency. The partial signals can also be generated digitally using algorithms, using analog circuitry, or can be selected from a database 28 of predefined partial signals. In one type of subtraction algorithm, filtered versions of the base signal are iteratively obtained (and may be subtracted from a base signal to ensure orthogonal spectral content) in order to create partial signals. The partial signal creator 42 can also generate the partial stimulation signals based upon calculations made upon data contained in the database 28, such as sensed calibration data or user inputted data. Partial signal generation may also include information about the number of leads activated during stimulation, the 2-dimensional positions of leads, the 2-dimensional inter-lead distances, the 3-dimensional positions of leads, the 3-dimensional inter-lead distances, the bipolar or unipolar activation mode for each lead, the 3-dimensional positions of grounds, and approximate impedances of the leads. The creator 42 can generate at least two partial stimulation signals based upon these calculations in order to produce approximately the desired electrical field summation signal in approximately one or more target tissue regions.

In any case, regardless of the methods used, once the partial signals are created these are then directed to their intended contacts 32 by the signal router component 44, which also may be realized within the stimulation subsystem 22 and which can contain digital-to-analog converters, filters, amplifiers, switches, charge balancing and biasing circuits, and mutliplexors, each of which can be separate components or which can be embodied into a specialized microchip. The components of FIG. 2*a*, can operate to provide continuous stimulation, or can be operated responsively, when sensing is combined with the illustrated steps of the method, and can activated iteratively, as might occur to provide different partial signals as therapy continues.

FIG. 2*b* shows a schematic representation of a method of using a system, such as that of FIG. 2*a*, that is designed to create partial signals that are to be used during stimulation. The first step is to create or select at least one stimulation signal 50 to be used during treatment. The stimulation base signal is then transformed into two or more partial signals 52 which are provided at each of two or more contacts 54.

During stimulation treatment, the actual summation of the partial signals within the target tissue will deviate from intended summation depending upon factors such as conductance, impedance, and the actual physical location and orientation of the electrodes. In one embodiment of a calibration method which is used, from time to time, the partial signals are adjusted based upon data which is sensed concurrent with stimulation. For example, a calibration signal which may be at least one partial signal is used to stimulate contact set "i" of N contacts 54, and data are sensed at contact set "j" 56, where sets "i" and "j" each include at least one contact. The sensed data allows empirical measurement of the electrical field and can be used to adjust the partial signals 58 so that the actual field vector more closely approximates the intended vector field in 3-dimensional space. This process can be iteratively repeated several times until the sensed signal is calculated to be within some tolerance level with respect to the intended signal. When stimulating with optical signals, the orientation and beam paths can be taken into consideration by the partial signal creator. In that instance, calibration used to adjust the partial signals 58 can be obtained using optical sensors that sense optical strengths of various light sources 56. When used with optical stimulation, in addition to the pattern of activation, different optical stimulation conduits may emit different frequencies of light at different locations, or different frequencies may be emitted from the same conduit at different moments of time.

FIG. 3*a* Shows a generic implantable stimulation device 10 that has a stimulation conduit which includes six electrical contacts (32A-F) that are implanted in the neural tissue 36 of a patient 38. The implantable stimulator 10 contains signal generating and computational circuitry, a power supply, sensors and other components which are commonly found generically in implantable stimulators such as has been described in U.S. Pat. No. 6,066,163, US2002/0072770, & US2004/017089. The stimulator may also be realized using the neurostimulators 10*a*, 10*b* shown in FIG. 1*a* and FIG. 1*b*. The stimulator device 10 can contain a general access port 6 which serves different functions in different embodiments, for example, the access port 6 can comprise a re-sealable septum which accepts a needle for replenishing fluids used in drug delivery, or the access port 6 can accept a control link from an external controller device. The device 10 can also contain a connection port 8 for connecting, for instance, to sensors 34 which can provide sensed data, or which can accept a signal from another implanted device for permitting two or more devices to collaboratively provide treatment. Although shown in a single region, the stimulation electrodes can be located in subsets provided in different regions of tissue, and may be realized in a unilateral, bilateral, or other treatment montage.

The present invention can assist in stimulating target tissue more precisely and can decrease side-effects of stimulation. In one general embodiment, stimulation occurs at two or more stimulation leads to create selected stimulation signals in approximately a target area, while stimulating with other signals in approximately non-target areas. The intended stimulation is thereby increasingly localized, since target areas are differentially stimulated with respect to non-target areas. In one more specific preferred embodiment, in a stimulation treatment, two or more electrical contacts each with stimulation signals comprised of frequencies which are separated by a specific range (e.g. differing by approximately 0.1 Hz to 20 Hz) can be used wherein each of the stimulation signals is output from a different contact, and wherein the contacts are sufficiently close that the fields can partially intersect. In one illustrative example, a 40 Hz stimulation signal is emitted from stimulation lead 32A, of FIG. 3*a*, and a 43 Hz stimulation signal is generated at stimulation lead 32C, which causes a beat frequency of 3 Hz to be induced in the tissue which is commonly stimulated by both stimulation leads. The spectral content of the partial signals can vary widely without changing the beat frequency. The vectors signal can contain energy from approximately 0.5 to 20 Hz, while the partial signals contain energy which is at least 25 Hz, and in that range, or the partial signals can contain energy between 80 and 200 Hz. In one preferred embodiment, the vector signal (or its rectified equivalent) contains a majority of its energy approximately below F1 Hz, while the partial signals (or their rectified equivalents) contain energy approximately above F2 Hz. In this embodiment, F1 and F2 are preferably both be 25 Hz. Using partial signals with very different spectral content than the vector signals may enable and the non-target regions to be stimulated in very different manners, such as with inhibitory stimulation, while the target regions are stimulated with excitatory stimulation. In another embodiment the partial signals contain energy approximately above 4 kHz and the non-target regions are "blocked" with inhibitory stimulation while the target regions are stimulated with interference fields that produce excitatory stimulation (Tai et al, 2005).

In order to decrease the risk, or amount, of tolerance and habituation, the spectral content of the vector signal can remain approximately constant, but can be generated using partial signals which change over time (thereby altering local field strengths and orientations of voxels, within the field, although the average field signal remains constant). For example, the two partial stimulation signals can simply be exchanged for two new signals which also generate a desired beat frequency as would occur if signals of 20 Hz and 24 Hz were exchanged for signals of 24 Hz and 20 Hz, or 22 Hz and 26 Hz. Alternatively, in another embodiment, the two carriers can be adjusted, for example, by periodically or continuously roving, stepping, or otherwise adjusting two stimulation signals so that the beat frequency is maintained within a specified frequency range, for example 0.1 Hz to 20 Hz. Roving a first stimulation frequency from 20 to 25 Hz while simultaneously roving a second stimulation frequency from 26 to 31 Hz will maintain a beat frequency of 6 Hz, in the anatomical area which receives the common stimulation. This type of stimulation strategy may not be prone to certain types of habituation or tolerance which may accompany simple constant 6 Hz stimulation. Further, if the stimulation protocol requires a change in the modulation rate of the vector signal, then the first partial signal could rove from 20 to 25 Hz, while the second signal concurrently roves from 26 to 27 Hz, causing the modulation rate of the beat signal to rove from 6 to 2 Hz as stimulation progresses. In other words, the spectral content of the vector signal can be held constant or varied while the spectral contents of partial signals are varied.

By way of illustration, by stimulating at two or more leads with two relatively high frequency carrier frequencies a beat frequency may be produced due to the interaction of the carriers in the neural tissue which is the target (labeled "T" in FIG. 3), while the higher frequencies will stimulate, with a continuous amplitude, the neural tissue which is not a target. The characteristics of the partial stimulation signals (higher frequencies of sinusoidal or pulse stimuli) can be selected as those which do not produce effects (e.g., below or above functional band-pass of tissue), or which produce different effects from the vector signal so that non-target neuronal tissue (which exists in the area labeled "NT" in FIG. 3) is differentially modulated by stimulation. In one embodiment, electrodes 32A and 32C can serve as anode and 32D can be cathode. Electrodes 32A, 32C, and 32D can also be multiple-lead bipolar stimulation leads. In an alternative embodiment, which is also intended to increase focal stimulation, stimulation occurs using two or more stimulation lead contacts (e.g., 32A and 32C) which stimulate at levels that would be subthreshold if provided individually, but which combine to produce super-threshold stimulation. The leads are positioned and oriented so that their fields combine to stimulate a target region (due to summation to produce adequate signal power, correct spectral content, orientation, or correct wave shape characteristics), while imposing subthreshold stimulation levels in adjacent areas. For example, stimulating with a 3V signal at a direct brain stimulation electrode implanted in the subthalamic nucleus (STN) will activate axonal elements in the STN, but can also activate structures as far as 4 mm from the electrode contact. Accordingly, in some embodiments, adjacent electrode contacts may be within approximately 2-6 mm when using strategies where the intention is for the stimulation fields to interact. Although FIG. 3a shows electrodes only configured along an x-y plane, it is obvious that the stimulation leads can be arranged in a 3-dimensional configuration, for improved shaping of the stimulation field. Accordingly, subthreshold stimulation can be used with correctly configured stimulation leads whose fields can summate to the extent needed for clinical efficacy (i.e. the fields of the partial signals combine to produce super-threshold characteristics) primarily in the region where neurostimulation is desired.

FIG. 3b illustrates an embodiment of an implantable stimulation system including a device 10 having 2 stimulation conduits which are electrode stimulation arrays 30 a, 30 b having 3 contacts each and located bilaterally along a patient's spine. The stimulation signals can be generated between contacts of the conduits or a distal conduit can serve as anode, cathode, or ground.

FIG. 3c illustrates an embodiment of a display screen 300 which is part of an external patient programmer which displays the shape, location, orientation and spectral characteristics of two or more stimulation fields of the partial signals and the vector field. Such a field might be created if the top and bottom contacts of the right stimulation array 30 b were cathode and the middle contact of stimulation array 30 a was ground, where the two partial signals flank a vector field which is contained between them. The ability to show the locations, orientations, spectral and temporal content, and shapes of both the partial signals and the vector signals is novel to prior art such as U.S. Pat. No. 6,393,325, incorporated herein by reference. The fields can also be shaped in calibration methods using phantom models or dyes which are activated by certain types of stimulation. The external patient programmer can contain a wide number of display screens, modeling software, and keyboard controls, and may be implemented as a laptop computer with telemetry means, as is well know to those skilled in the art.

Figure 4A:
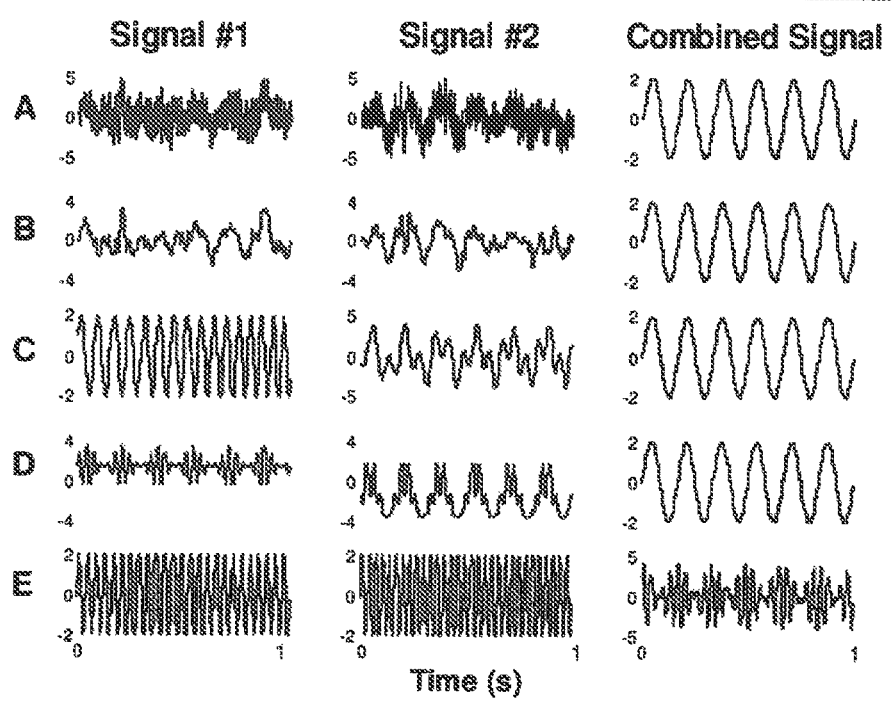
FIG. 4a shows example embodiments of partial signals, where signal #1 and signal #2 are partial signals which can be combined to form a vector signal which is a combined signal, and where the partial signals have a substantially different frequency content than the combined signal.

FIG. 4a shows several examples of partial signals. Each signal is part of a set which can be provided at 2 different leads. The sets of partial signals will combine to form a desired signal (a vector sum of the two partial signals) at or near the target tissue while stimulating with the partial signals outside of the target region. In row A, a wideband noise signal is shown in column 1, labeled "Signal #1", which when added to the "Signal #2" of column 2 will result to the "combined signal" shown in column 3. In row B, two pseudo-random low-pass signals are shown, which produce the combined field seen in column #3. Row C shows a chirp waveform with energies from 10 Hz to 20 Hz, as Signal #1, and also shows a Signal #2 which can be added to it to obtain the combined signal shown in column 3. In Row D, column #1 shows a rectified amplitude modulated carrier (i.e., there is a DC offset) where the carrier is 30 Hz and the modulation frequency is 6 Hz and Signal #2 shows the signal which must be added to obtain the combined signal shown in Column 3. In rows A-D, Signal 1 and Signal 2 may each serve as partial signals in order to induce the 6 Hz vector signal in the neural tissue commonly stimulated by both fields. The frequency content of the partial signals shown in columns 1 and 2 are unique from that produced in the combined signals of column 3. Accordingly, only those partial signals which produce desired effects can be selected to be included in the set of stimulation signals used during treatment, while the vector signal can be maintained. In Row E, a carrier frequency at 25 Hz comprises Signal #1, which when added to a 31 Hz carrier which is Signal #2, will result in a combined signal, which is the amplitude modulated beat waveform of Column 3. It should be noted that if Signal #1 has a positive DC offset and Signal #2 has a negative DC offset, that both signals can effectively exert a bias (e.g., to polarize their respective local non-target regions), while the target region near a ground electrode would experience a charge balanced field. By alternating the DC offset of the two partial signals, from time to time, the non-target areas would experience, over time, charge balanced stimulation as well. The utilization of DC biasing may also be important for improving transmission of energy from the electrode to tissue (Johnson et al, 2005).

Figure 4B:
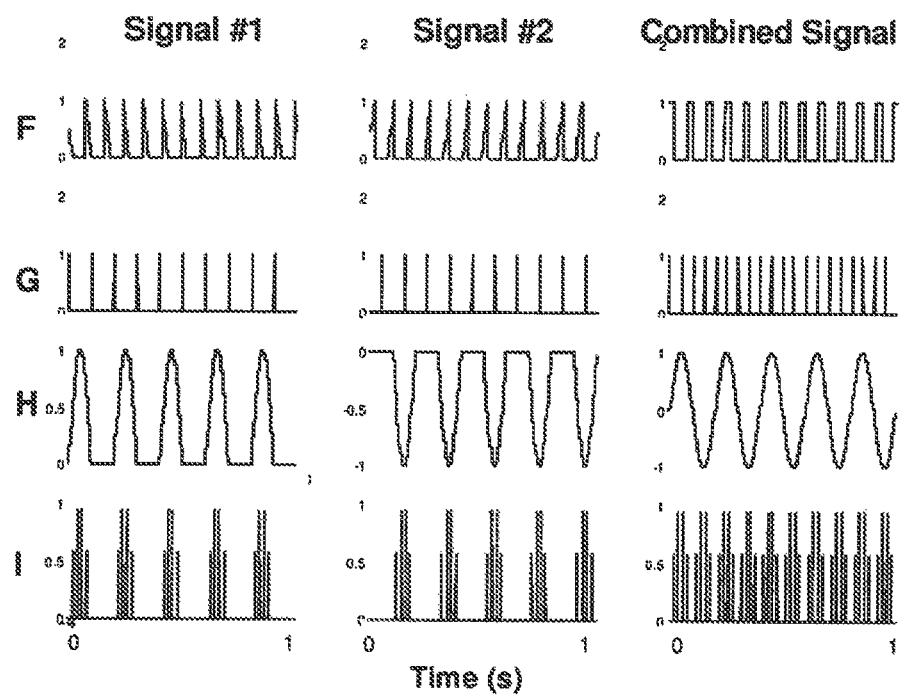
FIG. 4b shows alternative example embodiments of partial signals and vector signals, including pulsatile and modulated-pulse signals.

In FIG. 4b, an additional number of examples of partial signals are shown having certain characteristics relative to the those of the heterodyne signals of column 3, and offer objects and advantages not described in the prior art. In the first row of FIG. 4b, two saw-tooth pulses serve as the partial signals and these combine into a vector signal which is a square wave at the same frequency. This type of summation reflects an advantage that each cycle of a pulsatile waveform can be individually shaped to achieve desired results. In this case, the partial signal has pulses that are significantly briefer than the pulses of the summated signal. The time-energy characteristics of each of the pulses of the partial signals may therefore be subthreshold, while the vector field is super-threshold. In this case, partial signal 1 was subtracted from the combined signal in order to obtain partial signal 2, as may occur in the partial signal creator 42 or related methods 52, 82, 92. While only unipolar pulses are shown, bipolar pulses can also be implemented. In the second row, two pulse trains presented at F Hz, with a time lag, are combined to produce signal with a frequency of 2F. By changing the lag, different shapes of the pulse-train can be created. In one embodiment of the method of the invention, when multiple electrodes are used, each can fire in a non-burst manner with a time lag which produces a "burst-train", or paired stimulus with a specified interval, in the vector field. By tailoring the pulse patterns of the partial signals according to the properties of the target and non-target brain regions, any pattern of bursting, non-bursting, repetitive bursting, or other patterns as are known well in the art, can be differentially evoked. Additionally, in a treatment where higher frequencies are useful for preventing certain aspects of a disorder, while lower frequencies are useful for preventing others, then the lower frequencies can be used as the partial signals which stimulate certain areas and also heterodyne to produce faster frequencies in the target area.

In the third row two rectified sine-waves, with signal 2 inverted, are combined to produce a sine function over a larger range. This embodiment can be useful, for example, when either positive or negative stimulation at a particular electrode leads to unwanted side-effects, while the opposite is not true. Lastly, in the fourth row, two amplitude modulated pulse-width signals are shown having different offsets, and wherein the repetition rate (frequency of modulation) is doubled in the combined field.

Partial signals which are applied to the non-target region can be selected which are unlikely to stimulate that area in an undesired manner. A sufficiently fast carrier frequency may affect neural tissue only at the onset of a train because it exceeds the chronaxie of the tissue and is thus "invisible". Alternatively, carriers in selected high frequency bands (e.g., 2-6 kHz region) can excite, inhibit, or 'freeze' non-target regions, while this spectral content is not imposed in the target region. A pulse shape or duration, relative to its current or voltage, or the interpulse-interval or frequency can be set so that the field fails to entrain, or produce side-effects in, the NT area, while the vector field contains pulses that are entraining (e.g., FIG. 4B). Further, in paired pulse stimulation paradigms, the priming pulse can be provided at a different set of electrode contacts than the secondary pulse so that the area exposed to both pulses is increasingly localized to the target region. This is an advantage when the paired pulse paradigm is used to test the reactivity, or excitability, of a region, and is not described in the prior art.

The partial signals can be used with bipolar leads which are near each other, or can be generated by monopolar leads which serve as cathode or anode and which work in conjunction with a further lead that, for example, serves as ground. Each electrical contact may be a ground, isolated, mono-polar or bi-polar with respect to anode/cathode assignment. When operated in a bipolar mode, one of the lead contacts can serve as a ground or opposite polarity relative to the other contact. Alternatively, the shell of the stimulator 10 can serve as anode, cathode, ground or may be floating. Other combinations of polarities are possible as well, for example the shell of the stimulator 10 can be divided into different sections which are electrically isolated from each other, and when more than one stimulator 10 is used, each may have a shell that with a different electrical function, as may occur when the methods are implemented using stimulators such as the BION™. When multiple stimulators are used to provide the partial signals, these may have their grounds and power-sources connected to provide a common ground or power-source, or may be electrically independent.

In one embodiment, the partial signals in column 2 can be generated by subtracting the signals in column 1, from the signals in column 3 (within each of the respective rows for FIG. 4). In order to generate the appropriate signal #2, the neurostimulator can have an analog subtraction circuit or software routine which subtracts a given signal #1 from the desired base signal in order to generate signal #2, This operation can occur in within the partial signal creator 42 of FIG. 2a, which can utilize a specialized subtraction circuit or a software routine, which is part of the stimulation subsystem 22. The partial signal creator 42 can also have modules which take account of the geometry of the implanted leads with respect to each other and the neurostimulator, the tissue resistance, relative polarities, and ground contacts, with respect to the neurostimulator system, and which adjust the characteristics (e.g., amplitude) of the partial signals accordingly.

Another method of creating the partial signals is shown in FIG. 5a, and comprises the step of creating a low frequency base signal 60 which is intended as the vector signal which will be created by the summation of the partial signals in the stimulated tissue. The low frequency signal is added to a $1^{st}$ interference signal 62 a to create a first partial signal, and then added to a $2^{nd}$ interference signal to create a second partial signal 62 b, and this process is continued until all the partial signals are created. The interference signal can have a spectral content which is lower or higher than the base-signal, or can have approximately the same content, but may act to shape the partial signals so that these are somewhat different than the base signal (e.g., have a different shape). If the two partial signals do not need to have different spectral characteristics, then the $2^{nd}$ interference signal can simply be the $1^{st}$ interference signal, inverted. The interference signals can also simply be DC offsets and still offer advantages. If one electrode contact is provided with an arbitrary signal which has a positive DC offset and a second electrode contact has a different arbitrary signal with a negative DC offset of similar magnitude, then the tissue near the contacts may be polarized, while the sum field will merely have the vector field summation without DC offset. The partial signals are then each applied to a selected contact 74. Step 74 can occur continuously, repeatedly, responsively, or according to alternate strategy as dictated by the treatment program. The partial signals can be re-assigned to the same or different contacts in subsequent iterations. In step 74, the partial signals can be altered in magnitude and polarity based upon the 3D geometry of the electrodes, impedances, etc. Circuitry or software can model the field summation, and adjust the signals. Nodal, loop, mesh, current source density, finite element analysis, dipole, field distribution, impedance, and other types of analysis may be implemented in deriving the field model. As these types of analyses are computationally complex and may require human judgment, the analysis can be done offline, by medical personnel, and appropriate coefficients, mathematical transforms, and algorithms, which reflect the results of this analysis, can be uploaded to the device 10 and applied or implemented in step 62 during the creation of interference signals, or in steps 74, 78, or 82, or by another module or component of the stimulation subsystem In a simple model, the amplitude of a partial signal can be multiplied by constants related to the relative distance of each of the contacts and from sine and cosine functions evaluated upon the angles between a target and each of the electrode contacts, where contacts on opposite sides of a target will have angles 180 degrees apart and thus values which vary between 1 and −1, where the sign is ignored or included based upon the monpolar/bipolar mode, ground location, etc. This can be done for angles and distances along x, y, and z axes. In other words, the partial signals can each be mathematically back-projected from the neural target to their electrode source, or a virtual source located between the active contact and ground, in order to determine the waveforms used at the source. Additionally, as indicated by the arrow from step 74 to step 60, this process can be repeated if the low frequency base signal or the partial signals require replacement, for example, as dictated by the treatment program.

In FIG. 5b, a method is shown where a base signal with high frequency spectral content (e.g., a pulse train, paired-stimulus waveform, or arbitrary waveform) is created 76, and the interference signals are added to this signal 78 a, 78 b, to create partial signals that are applied at the contacts 74. A further method of providing the partial signals is shown in FIG. 6. The first step is to create a base stimulation signal 80, then create 2 or more partial signals 82 *a*, 82 *b* by modifying the base signal. Partial signals can be created by distributing the base signal spatially and/or temporally across the different contacts, and then applying each partial signal to a unique contact 74. As the figure shows, the steps 80, 82 and 74 can be repeated in a loop to provide adjustment of the partial signals and/or base stimulation signal. If the stimulation signal is to remain constant and only the partial signals are to be adjusted then only steps 82 *a*, 82 *b* and 74 need be accomplished. All three steps can occur approximately simultaneously and continuously. In other words, rather than providing the partial signals in a circular buffer which is filled in steps 82 *a* and 82 *b*, and which is then unchanged, the buffer can be updated wherein new data are read into the buffer as old data are transduced and provided at the contacts 32. Further, although partial signal 1 and partial signal 2 must be applied to specific contacts 32 in order to produce the vector field summation of the stimulation signal, the assignment of these signals to different electrode contacts can change somewhat easily. For example, after a specified amount of time the contacts for the first and second partial signals are switched (e.g., step 84 of FIG. 6). In one embodiment, after a specified duration, the signals used at lead contact 1 become signals for lead contact 2, and vice-versa. Local fields produced near the leads will change, while the vector field evoked in the target tissue will remain approximately the same (or may be inverted). It is obvious that when more than 2 partial signals are needed, steps 82 *a* and 82 *b*, for example, are extended to steps 82 *c*, 82 *d*, etc. (although not shown in FIG. 6) Depending upon the number of electrode contacts and their geometry, during this type of switching, the partial signals may be rescaled, phase shifted, or inverted in order to maintain the field summation in the target tissue which is intended by the treatment program. This strategy of re-assigning partial signals to selected contacts may be useful in overcoming some types of habituation or in decreasing unwanted side-effects which may be specific to a particular spectral or temporal component being emitted from a particular lead. When the stimulator 10 is an external TMS device, and instead of contacts, the stimulation is being produced by TMS coils which induce magnetic fields in the brain, the re-assignment of partial signals may be even more important since unlike implanted electrodes, the fields will affect the activity of significant portions of tissue outside of the target area. Re-assigning partial signals to different electrodes may be computationally less intensive than repeatedly creating new partial signals, which is an advantage when implemented by an implantable device, since it utilizes less power.

In yet another alternative embodiment, the assignment of pairs of partial signals can be altered in order to decrease habituation and in response to side-effects or provide other advantages. For example, if a 6 Hz stimulation field is found to be efficient in blocking seizures, but one set of partial signals is found to cause side effects, then this set can be exchanged for a different set of partial signals that result in the same final vector field. The patient or physician can participate in this selection, or the sets of partial signals can be determined automatically, as therapy progresses, based upon sensed data. Referring to FIG. 4*a*, if the set shown in row A produces side effects then the set shown in row B can be used since both will produce the same combined signal. Further, the frequency content of the partial signals can also be altered based upon considerations such as transmission of the signal through tissue, capacitance or resistance issues, efficacy to entrain or modulate tissue, or other factors. For example, if using carriers of 400 and 405 Hz provide better entrainment at 5 Hz than carriers of 200 and 205, then this prior set of carriers may be preferentially selected.

In another method of using partial signals to treat a disorder, (termed "trial and error method" or TAEM) two or more stimulation conduits are arranged sufficiently close that a portion of their fields will interact due to the size of the fields that will be created by two or more stimulation signals which will be used in treatment. A first partial stimulation signal is provided by the first conduit and is held constant. A second stimulation signal is then applied to a second conduit, and this field is adjusted until therapeutic benefit is obtained. In a preferred embodiment the first and second stimulation signals have different temporal or spectral characteristics. If the stimulation is therapeutic and there are no unwanted side effects then those two signals can be selected for use in therapy, while if side-effects occur then that set of partial signals is rejected. This process can iteratively repeated for different sets of two or more stimulation conduits, where subsets of the conduits can provide stimulation waveforms which are identical, similar or unique to each other. The settings which produce successful treatment therapy with no side-effects are stored in the database 28 for later use during the stimulation therapy. Additionally, the database 28 can store combinations which have been successful with similar electrode configurations in prior patients. When therapy is successful, the voltage or current of the stimulation settings can be increased in order to determine the limits at which the signals can be provided without the induction of side-effects. The database 28 can store sets of partial signals which are successful, and which are organized according to the current or voltage level which will be used so that if the patient increases the voltage or switches the partial signals, these changes will incorporate correct signals and amplitudes. In general the TAEM method can be summarized in a number of steps including: providing partial stimulation signals at two or more stimulators in a manner that will cause at least partial overlap of their fields; iteratively adjusting the stimulation parameters of at least one partial signal to determine successful partial stimulation signals (where successful signals provide at least some therapeutic benefit and relatively small side-effects); selecting those combinations of partial signals which proved successful and discarding the partial signals which were not successful; implementing successful signals in therapeutic treatment. As with the other methods which are described herein, the TAEM method can be improved by ranking the successful signals according their success, and biasing the treatment to select and apply the better signals according to their rank. The TAEM method can also be improved by performing a meta-analysis of the signals that were successful, and those which were not successful, and extrapolating, by computer program or other means, the characteristics of the vector fields that would have been created during stimulation. By analyzing the properties of the vector fields that would have been created for the successful signals and rejected signals, it is possible to infer the common characteristics of the vector fields which provided therapy. However, while possible, the TAEM methods described here are much less promising, and an labor intensive, relative to the other methods of the invention because there are almost an infinitely large assortment of possible combinations of partial signals.

In another method, termed the reverse-TAEM method, a partial signal is provided and alternated until it provides therapeutic benefit. When providing the partial signal causes unwanted side-effects, for instance as may occur when the voltage is increased to maintain symptom relief, the application of one or more other signals is provided in order to attempt to decrease side effects while maintaining therapeutic benefit. The TAEM and reverse-TAEM methods, and variations thereof can be accomplished during the initial setting of stimulation parameters, as well as periodically, as needed, during therapy by patient or physician. It is believed that in actual practice these types of trial and error strategy would produce significantly less benefit than other methods of this invention, because the number of possible combinations of partial signals are close to infinite, and information about the vector field signal is either ignored, or used in a very inefficient fashion.

General embodiments of methods of adjusting partial signals should rely upon knowledge of the base signal and vector field. Accordingly, in the first step different base signals are sequentially presented from all electrodes, and stimulation waveshapes which are best at reducing seizures can be determined, and become candidate stimulation base signals. However, if some of these candidate base signals utilize partial signals which produce side-effects, then sets of partial signals can be created and tested in order to determine if these are also effective at producing therapeutic effects while not producing unwanted side-effects of the base signals. Those partial signals which provide efficacious treatment, while not producing side-effects, can be selected for treatment. Additionally, it may be that certain sets of partial signals only produce unwanted side-effects when these are used with a specific range of voltage or current levels or even at particular leads. Accordingly, these partial signals may work well at lower levels or when assigned differently to the available leads. The selection of the partial signals can be based, in part, upon what voltage is required to produce the desired therapeutic effects. For instance, the partial signals of row A in FIG. 4a may work better at lower voltage levels while the set shown in row B works better at higher voltage levels. This type of relationship can be represented in the stimulation strategy implemented by the treatment program so that as the voltage increases, the partial signals are altered or substituted. For example, as voltage increases, the frequency content of the partial signals can also be increased, by switching to different sets of partial signals which have a higher frequency content. This can occur in a continuous or stepwise manner, and can occur based upon control laws. The selection and assignment of partial signals, or sets of partial signals, can therefore be selected based upon a characteristic of the treatment protocol such as overall voltage or current level. The different spectral and temporal characteristics of the partial signals can be modified according to overall stimulation level with consideration of the time-energy relationship of the stimulus to the average strength duration curve of the target cells. When partial signals are chosen in the context of these other considerations, this can occur according to "stimulation context rules". It is contemplated that as these techniques are increasing used, the stimulation context rules which work across a population, and even in relation to certain side-effects will become known, and these can be incorporated into the stimulation protocol.

FIG. 8, shows a further embodiment of a method used in the creation of partial signals which occurs by processing the base signals according to an algorithm. In the first step the stimulation signals are created 90 and these base signals are then processed 92 in order to produce modified signals which are used to stimulate at each of one or more contacts 94. The processing can rely upon, for example, a filtering algorithm which can filter the stimulation signals with different band-pass filters in order to create unique, and spectrally orthogonal, partial signals which will combine to approximate the base signal. Further, even if only one electrode contract is used for the stimulation, the step of processing the base signal 92 can provide a number of novel stimulation signals with a decreased amount of computational power or at least less specialized components or software modules. Instead of requiring a specialized algorithm for computing a chirp waveform (which may not exist in generic stimulation devices), a standard random-noise signal generator can be filtered by several band-pass filters over time, or by a programmable band-pass filter whose centre frequency is changed over time. Both random noise generation and digital filtering can be accomplished by components or algorithms common to generic implantable devices. The processing of step 92 can be accomplished by circuitry of the stimulation subsystem 22 and can occur according to stimulation protocols stored in the database 28 of the stimulator 10. Alternatively, all stimulation signals, and base or partial signals can be predefined by the user and stored in the database 28 to be accessed by control subsystem 20 in order to provide a stimulation protocol to the stimulation subsystem 22. Creation of the base signals and partial signals can both be accomplished by a function generator of the stimulation subsystem 22 and the signals can be selected or adjusted based upon the stimulation protocol and responsively.

In some applications where sensing is used in combination with stimulation, sensed data can lead to responsive stimulation or to changes in basal stimulation. The electrical artifact created by the stimulation makes sensing of physiological signals during the stimulation difficult because the stimulus artifact may be larger than the electrical signals which are produced by the brain. Further, when the stimulation occurs at the same frequency as the biological signal which is to be measured, it is very difficult to disentangle the sensed signal from the signal generated by the stimulator.

If the stimulation is chronically applied and the neurostimulator also senses EEG to predict/detect the onset of seizures, then the stimulation signal should be factored into the detection algorithm (i.e., subtracted or removed from the sensed data). When the stimulation occurs using a signal having only high frequency spectral content e.g., 180 Hz pulse train, then the stimulation signal may not interfere with, or may be easily removed from, the endogenous slower frequencies of the EEG which is sensed. However, when the stimulation occurs at 3 or 8 Hz, then this can be intertwined with endogenously generated brain activity and can affect the detection algorithms. When the stimulation signal is created using sensed activity so that its frequency content changes over time, then a digital filter may be varied to remove the stimulation signal from the incoming EEG. Additionally, adaptive filters, such as Kalman filters, or independent component analysis, can be used to remove the energy related to the stimulation signal from the sensed data.

Two additional types of strategies can assist in enabling sensing to approximately co-occur with stimulating as will now be described. Firstly, using a modulation signal (e.g. 20 Hz) with a carrier signal which has a much higher frequency content (e.g., 1000 Hz) can cause the stimulated tissue to be stimulated at 20 Hz, while the stimulus energy exists at 980, 1000, and 1020 Hz. If the filter of a sensor has a low-pass cut-off of 250 Hz, then the energy which is sensed at 20 Hz, should be primarily physiological, and will only be contaminated by rectification of the stimulation signal. Secondly, using partial signals that have spectral content which is in a different range than the signal which is to be sensed can enable certain types of sensing to occur. For example, using the partial signals in Row A or E of FIG. 4a, and filtering the sensed data with a low-pass filter which is sufficiently above the primary frequency component of the vector field so that this may be measured, should enable separation of stimulus artefact from a biological rhythm at the same frequency as the modulation of the vector field, since the heterodyne signal should not exist much outside of the target tissue. In one example, the stimulation electrodes and the sensing electrodes are located sufficiently distal that the vector field is not sensed by the sensing electrode. In that instance the sensing electrode is implanted with some consideration of the electrode geometry of the stimulation contacts. In cases where the strategies just described do not permit separation between stimulus artefact and the physiological signal, the sensing can occur in a different modality. For example, optical, thermal, chemical or other sensing can occur which will not be compromised by simultaneous electrical stimulation.

Stimulation Strategies and Temporal Partial Signals.

Rather than distributing a base signal into partial signals which concurrently stimulate across a number of leads, partial signals can be provided in a consecutive manner with partial temporal overlap or no overlap. In one example of this method, shown in FIG. 9 a method of providing stimulation uses a multiple lead stimulator in which the base signal is separated into partial signals that are distributed across multiple contacts located either on different leads, or on a multi-contact lead, and the partial signals are temporally distributed across the contacts. In the simplest form, a base signal can be divided into, for example, N partial signals and each of these partial signals is used to stimulate particular contacts of N possible contacts. Again, characteristics such as polarities and magnitudes may be altered according to the relative position of the contacts with respect to the target tissue, and/or the energy transfer characteristics of the contacts (e.g., impedances), so that the stimulation signal in the target tissue approximates the base signal as if it had been delivered from a particular lead. Each of the N partial signals can be delivered at a different time, or can have some overlap in time with other partial signals being delivered in order to additionally provide for field summation. This strategy can have several advantages. Because the stimulation is generally provided by assigning the stimulation signal to different leads, at different moments in time, the signal which is provided at any particular lead may repeat, or may be unique, even if the stimulation signal itself, integrated across time and leads, remains constant. Accordingly, temporally distributing the base signal into sub-signals which are assigned to different leads is one method of decreasing the risk of adaptation. This type of strategy may also reduce side-effects, since it can stimulate with a pulse train burst in the neural target, while the individual contacts stimulate with pulses in a non-burst manner. In an example of a preferred embodiment a 3 Hz sinusoidal frequency is distributed to each lead of a multiple lead stimulator (or contact of a multi-contact lead), which stimulates for only a portion of the base signal. These segments of the base signal are termed a "sub-signals". The summation of the sub-signals across all the leads will result in the base stimulation signal with respect to target tissue, but not with respect to surrounding tissue. In FIG. 9, a signal is temporally divided into N sub-signals signals 100. In the next step 102, each sub-signal is assigned to M contacts, and then these M contacts consecutively provide the stimulation signal to the target neural tissue 104. Rather than consecutively activating single contacts, two or more of the M contacts can provide stimulation at the same time, and when these contacts are close enough that their fields can summate, then the sub-signals are also considered to be partial signals which will produce a vector field approximating a base signal.

An example which illustrates this method is now more specifically described. A 3 Hz sinewave signal can be distributed into 6 sub-signals which are distributed across 6 leads, such that each sub-signal stimulates for half a cycle of the stimulation function. Although none of the leads actually stimulate using the stimulation signal, the 6 leads are activated with the appropriate lag such that the generated signal, from the perspective of the target neuronal population, is the reconstituted base signal. This approach can be utilized when using any stimulation signal, regardless of whether this is a burst stimulus, pulse-train, noise or a sinusoidal signal. Because each lead will stimulate using a sub-signal, the stimulation protocol can be adjusted so that each subsequent sub-signal emitted by a specific lead will always be unique from the prior signal which it generated. For example, each lead may stimulate using a sub-signal which represents ¾ of a cycle of the stimulation signal, so that each subsequent stimulation from each electrode will occur with a new phase, In this example, the interval between stimulation of consecutive contacts could be 125 msec and the following leads will output the following cycles of the stimulation signal in units of wavelength 1=0-0.75 (i.e. the first electrode outputs 75% of a cycle of the stimulation frequency), 2=0.75-1.5, 3=1.5-2.25, 4=2.25-3, 5=3-3.75, 6=3.75-4.5, 1=4.5-5.25, 2=5.25-6, etc. Using this type of distributed stimulation paradigm may decrease the effects of local tolerance, electrical impedance/capacitance, or emergence of side-effects due to a specific wave-shape, frequency of spectral energy, or other characteristic of the stimulation signal, being emitted from a particular source.

Additional Spectral Considerations

Small changes in spectral characteristics of arbitrary signals as well as pulse-trains can have significant effects in terms of providing therapeutic benefit of neurostimulation. The electric fields generated by the neurostimulation leads are dependent on both the shape of the electrode and also on the electrical conductivity of the tissue. In the central nervous system conductivity is both inhomogeneous (dependent on location and the type of cells in that location) and anisotropic (dependent on direction or orientation of the cells with respect to the stimulation field). The inhomogeneity and anisotropy of the tissue around the neurostimulation electrodes can alter the shape of the electric field and the subsequent neural response to stimulation. The result of the neurostimulation is complicated further by the effects that the fields will have on the individual neurons. The second derivative of the extracellular potentials along each process will invoke both transmembrane and axial currents that will be distributed throughout the neuron (a can be computed from the cable equation). In turn, each neuron exposed to the applied field will be affected by both inward and outward transmembrane currents and regions of depolarization and hyperpolarization. These types of complex responses to stimulation have been examined and verified in a large number of experimental preparations demonstrating the differences between anodic, cathodic, and bipolar stimulation with respect to activating and blocking neural activity using extracellular stimulation (McIntyre & Grill, 2002).

Accordingly, when generating a vector field by using at least two partial signals from different electrodes, the induced electrical potentials will be different than if both electrodes stimulated using a signal represented by the vector field (i.e., stimulating with two partial signals that create a beat frequency may induce different effects than would occur by providing that frequency from two or more electrodes). These variations can effect energy transmission and entrainment and/or can specifically affect certain neurons in order to compensate for the limited resources available when working with implanted systems which rely upon fields that are generated from neurostimulation electrodes of fixed locations.

Spectral considerations are even more important when stimulating using extra-cranial electrical or magnetic stimulation. A stimulation signal which utilizes spectral energy with a center frequency of between approximately 200 and 1000 Hz, may produce very different effects than when using a center frequency of between approximately 1 and 100 kHz. Both of these frequency ranges can be used to deliver stimulation signals which are used as base or partial signals. In a preferred embodiment, one or more band-pass noise stimuli are used which may differ widely in their spectral content, such that the partial signals, or the vector field is modulated between 0.5 and 20 Hz. The term "energy between approximately 0.5 and 20 Hz" may be understood, in some embodiments, as a band of energy which may span 1 Hz or more. For example, the band of energy may span approximately 4 Hz and be centered at 6 Hz, and may be asymmetrical, with slightly more energy at the 2 higher frequencies of the band.

Using Scores and Context Rules to Provide Neurostimulation.

In addition to the novel methods and signals just described, the current invention contains novel methods for providing or altering stimulation in response to sensed data. These methods can be used both with conventional stimulation techniques or with partial signals. In the prior art, if analysis of sensed data results in the detection of an event then some type of change occurs, such as initiating or modifying neurostimulation. As long as an event is detected, this change may often occur identically, without consideration of: 1. the size, type, or location (e.g., where the event is detected with a larger amplitude by particular electrodes) of the event; 2. whether the event is sensed at one or many of the sensors, and 3. the distances between the sensors, which may be relatively close or widely separated In one embodiment of the present invention sensed data are processed to produce scores, and stimulation can be applied according to these scores. Additionally, partial signals, and sets of partial signals, can be deemed to be successful, selected or rejected, and even ranked according to scores. The scores can reflect an attribute of the sensed data such as the absolute size or type of activity at one or more sensors, the number of sensors where the event is detected, the relative size of the event at each sensor, the relative size of an event compared to the EEG spectral power in selected frequency bands, coherence or correlation between different sensors, for example, during the time of the event compared to when the event is not occurring. One or more characteristics of an event (e.g., the amplitude of a seizure), is measured in the sensed data in order to produce a score. The score can be based upon a single characteristic of the sensed data at a single lead, or can be multivariate where the score is determined as a function of several predefined dimensions along which neural activity is assessed (each of which may be reflected in a term in the score equation). Scores can also be generated based upon an evaluation of sensed data which may occur by combining two or more sub-scores. Scores can reflect events or states related to the disorder, and can be evaluated in relation to past scores past scores (e.g., compared to past scores). When evaluation of processed data is used to generate scores, this process can utilize context rules.

Context rules evaluate an event within a temporal, spatial or other context in which it has occurred. For example, if the detected event has been detected within the prior 1-minute period, then the score can be doubled. The context rules can be used to enable the score to be modified based upon different aspects of the sensed data which are at least partially independent from the detected event. For example, scores can be based upon EEG measures sensed from one or more sensors related to the QEEG profile, reflecting different states of the brain, based upon the amount of at least one chemical substance sensed at one or more sensors, or the relative amounts of substances, the time of day, or the number of events detected within a specified time period.

Different stimulation parameters can be selected or adjusted in relation to the scores. For example, a score from 1 to 3 may cause the amplitude of the stimulation signal to be increased from 1 to 3 volts, while scores of greater than, for example, 4 may indicate a qualitatively different type of activity has been detected and can cause completely different stimulation signals or strategies to be used. When the score is a multivariate measure, different types of activity can lead to a similar score. The score can reflect both the characteristics of an event as well as the brain-state in which it occurs. In one embodiment of the method a first stimulation signal stimulates at least one target area according to a predefined treatment protocol, and sensed data are sensed at one or more sensors. A processing module processes the sensed data to generate a score, and a second stimulation signal is then provided according to a stimulation protocol that is determined by the score. In this method, medical or physiological events or states aren't themselves evaluated, but rather characteristics of the brain system itself is evaluated and the scores modulate stimulation in a continuous or responsive manner.

In a further embodiment basal stimulation is provided and sensed data is obtained according to a sensing protocol. The sensed data is then processed to generate both a normal and an abnormal score. For example, data is submitted to a first equation which produces a normal score based upon evaluation of one or more measurements of the data, and a second equation which produces an abnormal score based upon a different evaluation of which also uses one or more measurements. Stimulation is provided only when the two scores meet some criteria relative to each other. For example, the abnormal score must be twice the normal score for stimulation to occur. A partial embodiment of this method utilizes a discriminant analysis algorithm which provides the probabilities (i.e., scores) that the sensed data should be classified as normal or abnormal. In this case, stimulation may only occur when the abnormal score is above a specified level, or has a specified relation to the normal score.

In another embodiment basal stimulation is provided and sensed data is obtained according to a sensing protocol. The sensed data is then processed to generate either a normal or an abnormal score. Stimulation is provided only when a meta-analysis of the score meets some criterion. For example, abnormal scores must occur a specified number of times, possibly within a specified duration, before stimulation will occur. In a variant of this method, a score is derived which is neither normal nor abnormal, but which must be above a specified threshold in order for stimulation to occur and the scores are computed upon sequentially sensed data. In another variant, the sum of the scores over a specified period must be above a criterion in order for stimulation to occur. In other words, the meta-analysis may combine the scores in a wide variation of manners as is dictated by the treatment program.

In another embodiment, basal stimulation is provided, and responsive stimulation can occur according to control laws. For example, one type of basal stimulation can occur generally during treatment in order to prevent epileptic activity, and sensed data can be processed by a control circuit which generates a responsive stimulation signal according to control laws. In one embodiment, the control laws would cause the amplitude of a responsive signal to be adjusted based upon the amplitude of a selected characteristic brain activity, such as a temporal pattern of brain activity.

In a further alternative method, basal stimulation therapy is provided, and responsive stimulation occurs when events are detected. In this method, the characteristics of the treatment program are adjusted or selected partly or completely based upon a state index, which is independent of the characteristics of the event which was detected. For example, the state index can reflect different states of the brain, such as sleeping, awake, anxious, or drowsy. These states can be defined based upon different EEG and QEEG profiles which normally exist during these states in the patient. While the event triggers responsive stimulation, the characteristics of the stimulation are modified by aspects of the send data that are at least partially independent from the detected event.

In another example of the method, basal stimulation therapy is provided, and responsive stimulation occurs due to processed data. In this method, the characteristics of the treatment program are adjusted or selected partly or completely based upon a processed data. Processed data can result in a score, an index related to measuring chaos, complexity, various Hjorth parameters, equations including weighted scores from previous results, and other types of measures and results. In one example, the analyses of the processed data is altered by at least one of the prior events which had been detected, or scores which had been generated.

In a further example of the method, basal stimulation therapy is provided, and responsive stimulation occurs due to evaluation of trigger events. In this method, a trigger event can cause responsive neurostimulation to occur. In an alternative method, two trigger events must occur for responsive neurostimulation to occur, and a further restriction may be that these must occur in a specific order, or within a specified amount of time, or both. Additionally, an event #2 may only be evaluated if a different event, such as event #1, previously occurred. For example, a certain type of activity related to a seizure may only be evaluated, and possibly result in responsive neurostimulation, if another event occurred relatively recently. This type of strategy may be defined in a function wherein the difference in time between 2 events, which are related to epilepsy, is increased in relation to the size of that activity, so that 2 larger events may occur with a greater lag than two smaller events in order to lead to responsive stimulation.

In yet another example of the method, basal stimulation therapy is provided, and responsive stimulation occurs when evaluation of sensed data indicates that continuous stimulation is not sufficient. For example, sensed data may indicated that a change in state has occurred wherein the new state is more likely to produce seizures, and requires a different type of stimulation to occur until the state returns or reverts to a different state.

Transcranial Magnetic Stimulation Applications.

Figure 10:
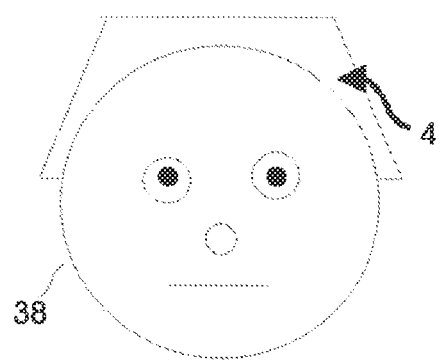

FIG. 10 shows a device 4 for providing transcranial magnetic stimulation and responsive transcranial magnetic stimulation (rTMS) to a patient 38. Device 4 can be similar to that as been described in US20030028072 entitled low frequency magnetic neurostimulator for the treatment of neurological disorders' (the '072 application), which proposes a device which is a head-mounted structure containing means to provide TMS from at least 2 sources. Treatment entails applying energy in a range below approximately 10 Hz to the patient's brain tissue. An implantable embodiment where direct electrical stimulation is used, is also described. Similar to this and other prior art, the present invention can be head mounted, exist as a small portable device, or may be configured to stimulate any part of a patient's body.

The methods and systems described herein offer advantages over this and other prior art methods of using stimulation such as low frequency stimulation provide using either implanted and external sources. The characteristics of the stimulation signals can be adjusted according to endogenous rhythms in the brain in order to increase the efficacy of treatment can be used in the rTMS treatment. Accordingly, the pulses, carrier or modulation waveforms of the treatment can be matched to, or divergent from, spectral characteristics sensed within the patient's brain or body (by sensors which are implanted or external to the patient, and which may exist within other instruments). This type of treatment could be enabled, for example, using an EEG amplifier and an electrode attached to the surface of the patients head. The amplifier may be physically disconnected from the electrode during periods of pulsed magnetic stimulation so that currents are not induced in the electrode wire. Optical probes, placed on the scalp, could also be used. The sensed data can be obtained prior to treatment or in the periods between treatment pulses, which may occur in a regular, periodic manner or in response to evaluation of the EEG that is sensed. The use of partial signals, having unique spectral or temporal characterstics, can also be utilized by configuring the geometry of two or more stimulation coils appropriately with respect to the intended neural target. Since fields from external coils must travel through intervening tissue in order to arrive at their targets, the use of partial stimulation signals is well suited to the rTMS application.

When the rTMS treatment is used for treating disorders such as depression, the stimulation is can be primarily directed to the frontal areas of a patient's brain, and within the frontal areas the treatment may be primarily lateralized to either the left or right hemisphere, although both hemispheres can be treated. In one embodiment, when treating disorders such as depression, the rTMS stimulation can be pulsed or modulated primarily above 20 Hz, although the vector field may be modulated at a rate below this frequency. The use of partial signals and vector fields may be applied to TMS applications including induction or facilitation of anesthesia either with or without concurrent drug therapy, electrochemotherapy, therapies that affect the permeability of the blood brain barrier, applications of TMS to stroke recovery and other types of adaptation, the modulation of cellular and metabolic processes, and other therapeutic methods and applications.

In one embodiment, the external stimulation can occur using one or more of electric, electromagnetic, optical, laser, or RF field stimulation from outside the head. Stimulation may utilize spectral energy in the ultra-high frequency (UHF) range, for example, 400 kHz to 150 mHz in its carrier signal. Frequencies in this range may be provided to enable certain benefits, such as better transmission of energy from the stimulator into the brain of the patient or better entrainment of the brain by the stimulation, as long as considerations are taken to avoid tissue damage. This carrier signal can be pulsed or modulated at brain frequencies from, for example, 0.1 Hz to 40 Hz, or higher ranges if areas such as the cerebellum, reticular activating system, or brainstem, are to be stimulated. By adjusting the modulation of the energy so that this matches the internal rhythms of the brain, either in aspects of temporal or spectral content, or phase or delay with respect to endogenously generated rhythms, the rhythms can be augmented (Bawin et al, 1973) or diminished. Treatment strategies may also select neurostimulation signals that are at different frequencies than those which occur endogenously, in order to provide certain types of treatment or in order to avoid interfering with certain endogenous processes.

Treatment.

When using the stimulation methods described herein, targets for stimulation can be any part of an organism, for example, targets may be neural, vascular, in the brain spinal cord, heart, digestive system, or muscle or organ. Targets used in the treatment of different disorders (e.g., epilepsy, migraine, psychiatric, neurodegenerative, memory, eating, pain, sleep, mood, anxiety, movement disorders, and tremors) may include, but not be limited to the one or more regions of the hippocampus, cortex, especially the frontal or motor cortex, brainstem, thalamus, and spinal cord, or at least one nerve structure comprises at least one of the vagus nerve, a trigeminal nerve, a branch of the trigeminal nerve, a trigeminal ganglion, an ophthalmic nerve, a maxillary nerve, a mandibular nerve, a greater occipital nerve, a lesser occipital nerve, a third occipital nerve, a facial nerve, or a glossopharyngeal nerve.

The stimulation methods described herein can be used to stimulate tissue in order to modulate electrical, chemical, metabolic, or other types of activity, as well as cellular and developmental processes. The methods and systems for generating electrical fields can be applied to therapies and procedures related to growth and differentiation of cells (e.g., pre/post-implantation procedures related to stem or fetal cells), including neural differentiation which is induced by electrically stimulated gene expression (Mie et al, 2003). Further, the methods and systems can be used in conjunction with treatments such as chemotherapy in order to potentiate the response to or uptake of chemotherapeutic agents or can be used independently as an anti-cancer therapy where electrical treatment of malignant tumors and neoplasms is provided by applying vector field stimulation approximately to affected tissue. Additionally the methods and systems can be used to modulate gene transfection, or alter the uptake of drugs by cells (e.g, electroporation, electropermeabilization, DNA electrotransfer) and can also be applied to modulate cellular growth and proliferation (Miklavcic et al., 1998; Faurie et al, 2004; Pucihar et al, 2002; Ciria et al, 2004; Cucullo et al., 2005). In some of these cases, great advantage may be obtained from using partial signals when stimulating focally in the 0.1 Hz to 20 Hz range, with respect to decreasing unwanted side-effects and assisting in patient tolerance to treatment. The stimulation can be used to alter cellular functioning, particularly protein synthesis, and alter synaptic transmission by modulating the production of neurotransmitters (Cucullo et al, 2005; Benabid & Wallace, 2005). The techniques can be used for wound healing, bone repair, and modulation of cellular activity and can also be used for prophylactic treatment. Further, the methods and systems can be used in dermatological treatment and cosmetic applications such as tissue reshaping and skin tightening, for example, by causing controlled patterns of damage, electroporation, thermal induction, wound healing, and collagen growth in selected tissue areas, such as skin, muscle, and fat. The systems and method can also be used to stimulate drugs or drug release, for example drugs stored within nano-particles which release these drugs when triggered by specific types of energy. The creation and utilization of partial signals described herein can be provided by implanted electrodes, or by optical transducers, or by external stimulation devices such as rTMS devices.

The stimulation methods and systems of the current invention can be used in conjunction with priming techniques. For example, subthreshold or super-threshold stimulation can occur prior to, stimulation with any of the described techniques in order to facilitate, enhance, or diminish the response to the subsequent stimulation (e.g. Lyer et al, 2003). Likewise, post-stimulation modulation signals can be paired with stimulation signals in order to modulate, enhance, or diminish the response to the prior stimulation.

The contents of all prior art examples cited in this specification and all scientific and technical references, are hereby incorporated by reference as if recited in full herein. In the body or claims of this application, even when methods have steps which have been assigned letters, the steps may occur sequentially in the order indicated by the letters, or certain steps may occur approximately simultaneously, or in an interleaved fashion, with other steps. The headers for various sections of this application, such as "Background" or "Treatment", are intended to be descriptive only, and do not limit the scope of the material which is provided in these sections, in any way.

REFERENCES

Barr R C & Plonsey R (1992). Electrophysiological interaction through the interstitial space between adjacent unmyelinated parallel fibers. *Biophys J* 61, 1164-1175.

Basser P J & Roth B J (2000). New currents in electrical stimulation of excitable tissues. *Annu Rev Biomed Eng* 2, 377-397.

Bawin S M, Gavalas-Medici R J & Adey W R (1973). Effects of modulated very high frequency fields on specific brain rhythms in cats. *Brain Res* 58, 365-384.

Benabid A L, Wallace B, Mitrofanis J, Xia C, Piallat B, Fraix V, Batir A, Krack P, Pollak P & Berger F (2005). Therapeutic electrical stimulation of the central nervous system. *C R Biol* 328, 177-186.

Brasil-Neto J P, de Araujo D P, Teixeira W A, Araujo V P & Boechat-Barros R (2004). Experimental therapy of epilepsy with transcranial magnetic stimulation: lack of additional benefit with prolonged treatment. *Arq Neuropsiquiatr* 62, 21-25.

Bruet N, Windels F, Bertrand A, Feuerstein C, Poupard A & Savasta M (2001). High frequency stimulation of the subthalamic nucleus increases the extracellular contents of striatal dopamine in normal and partially dopaminergic denervated rats. *J Neuropathol Exp Neurol* 60, 15-24.

Bruet N, Windels F, Carcenac C, Feuerstein C, Bertrand A, Poupard A & Savasta M (2003). Neurochemical mechanisms induced by high frequency stimulation of the subthalamic nucleus: increase of extracellular striatal glutamate and GABA in normal and hemiparkinsonian rats. *J Neuropathol Exp Neurol* 62, 1228-1240.

Cemazar M, Miklavcic D, Mir L M, Belehradek J, Jr., Bonnay M, Fourcault D & Sersa G (2001). Electrochemotherapy of tumours resistant to cisplatin: a study in a murine tumour model. *Eur J Cancer* 37, 1166-1172.

Ciria H C, Quevedo M S, Cabrales L B, Bruzon R P, Salas M F, Pena 0 G, Gonzalez T R, Lopez D S & Flores J M (2004). Antitumor effectiveness of different amounts of electrical charge in Ehrlich and fibrosarcoma Sa-37 tumors. *BMC Cancer* 4, 87.

Cucullo L, Dini G, Hallene K L, Fazio V, Ilkanich E V, Igboechi C, Kight K M, Agarwal M K, Garrity-Moses M & Janigro D (2005). Very low intensity alternating current decreases cell proliferation. *Glia* 51, 65-72.

D'Arcangelo G, Panuccio G, Tancredi V & Avoli M (2005). Repetitive low-frequency stimulation reduces epileptiform synchronization in limbic neuronal networks. *Neurobiol Dis* 19, 119-128.

Deurloo K E, Holsheimer J & Bergveld P (2001). The effect of subthreshold prepulses on the recruitment order in a nerve trunk analyzed in a simple and a realistic volume conductor model. *Biol Cybern* 85, 281-291.

Dinner D S (2002). Effect of sleep on epilepsy. *J Chn Neurophysiol* 19, 504-513.

Faurie C, Phez E, Golzio M, Vossen C, Lesbordes J C, Delteil C, Teissie J & Rols M P (2004). Effect of electric field vectoriality on electrically mediated gene delivery in mammalian cells. *Biochim Biophys Acta* 1665, 92-100.

Gerloff C, Cohen L G, Floeter M K, Chen R, Corwell B & Hallett M (1998). Inhibitory influence of the ipsilateral motor cortex on responses to stimulation of the human cortex and pyramidal tract. *J Physiol* 510 (Pt 1), 249-259.

Gerloff C, Corwell B, Chen R, Hallett M & Cohen L G (1997). Stimulation over the human supplementary motor area interferes with the organization of future elements in complex motor sequences. *Brain* 120 (Pt 9), 1587-1602.

Goodman J H, Berger R E & Tcheng T K (2005). Preemptive low-frequency stimulation decreases the incidence of amygdala-kindled seizures. *Epilepsia* 46, 1-7.

Graham-Jones S, Holt L, Gray J A & Fillenz M (1985). Low-frequency septal stimulation increases tyrosine hydroxylase activity in the hippocampus. *Pharmacol Biochem Behav* 23, 489-493.

Gray J A, Araujo-Silva M T & Quintao L (1972). Resistance to extinction after partial reinforcement training with blocking of the hippocampal theta rhythm by septal stimulation. *Physiol Behav* 8, 497-502.

Hoekema R, Venner K, Struijk J J & Holsheimer J (1998). Multigrid solution of the potential field in modeling electrical nerve stimulation. *Comput Biomed Res* 31, 348-362.

Holsheimer J, Nuttin B, King G W, Wesselink W A, Gybels J M & de Sutter P (1998). Clinical evaluation of paresthesia steering with a new system for spinal cord stimulation. *Neurosurgery* 42, 541-547; discussion 547-549.

Holsheimer J & Struijk J J (1991). How do geometric factors influence epidural spinal cord stimulation? A quantitative analysis by computer modeling. *Stereotact Funct Neurosurg* 56, 234-249.

Holsheimer J, Struijk J J & Rijkhoff N J (1991). Contact combinations in epidural spinal cord stimulation. A comparison by computer modeling. *Stereotact Funct Neurosurg* 56, 220-233.

Holsheimer J, Struijk J J & Tas N R (1995). Effects of electrode geometry and combination on nerve fibre selectivity in spinal cord stimulation. *Med Biol Eng Comput* 33, 676-682.

Holsheimer J & Wesselink W A (1997). Effect of anode-cathode configuration on paresthesia coverage in spinal cord stimulation. *Neurosurgery* 41, 654-659; discussion 659-660.

Holsheimer J & Wesselink W A (1997). Optimum electrode geometry for spinal cord stimulation: the narrow bipole and tripole. *Med Biol Eng Comput* 35, 493-497.

Holt L & Gray J A (1983). Proactive behavioral effects of theta-blocking septal stimulation in the rat. *Behav Neural Biol* 39, 7-21.

Holt L & Gray J A (1985). Proactive behavioral effects of theta-driving septal stimulation on conditioned suppression and punishment in the rat. *Behav Neurosci* 99, 60-74.

Irnich W (1999). Paradigm shift in lead design. *Pacing Clin Electrophysiol* 22, 1321-1332.

Iyer M B, Schleper N & Wassermann E M (2003). Priming stimulation enhances the depressant effect of low-frequency repetitive transcranial magnetic stimulation. *J Neurosci* 23, 10867-10872.

John E R, Leiman A L & Sachs E (1961). An exploration of the functional relationship between electroencephalographic potentials and differential inhibition. *Ann N Y Acad Sci* 92, 1160-1182.

Kasteleijn-Nolst Trenite D G & Vermeiren R (2005). The impact of subclinical epileptiform discharges on complex tasks and cognition: relevance for aircrew and air traffic controllers. *Epilepsy Behav* 6, 31-34.

Katayama Y, Yamamoto T, Kobayashi K, Oshima H & Fukaya C (2003). Deep brain and motor cortex stimulation for post-stroke movement disorders and post-stroke pain. *Acta Neurochir Suppl* 87, 121-123.

Kim Y, Zieber H G & Wang F E (1990). Uniformity of current density under stimulating electrodes. *Crit Rev Biomed Eng* 17, 585-619.

Kinoshita M, Ikeda A, Begum T, Yamamoto J. Hitomi T & Shibasaki H (2005). Low-frequency repetitive transcranial magnetic stimulation for seizure suppression in patients with extratemporal lobe epilepsy-A pilot study. *Seizure* 14, 387-392.

Kinoshita M, Ikeda A, Matsumoto R, Begum T, Usui K, Yamamoto J, Matsuhashi M, Takayama M, Mikuni N, Takahashi J, Miyamoto S & Shibasaki H (2004). Electric stimulation on human cortex suppresses fast cortical activity and epileptic spikes. *Epilepsia* 45, 787-791.

Kossoff E H, Ritzl E K, Politsky J M, Murro A M, Smith J R, Duckrow R B, Spencer D D & Bergey G K (2004). Effect of an external responsive neurostimulator on seizures and electrographic discharges during subdural electrode monitoring. *Epilepsia* 45, 1560-1567.

Kovner R & Stamm J S (1972). Disruption of short-term visual memory by electrical stimulation of inferotemporal cortex in the monkey. *J Comp Physiol Psychol* 81, 163-172.

Krnjevic K, Morris M E & Reiffenstein R J (1982). Stimulation-evoked changes in extracellular K+ and Ca2+ in pyramidal layers of the rat's hippocampus. *Can J Physiol Pharmacol* 60, 1643-1657.

Kuncel A M & Grill W M (2004). Selection of stimulus parameters for deep brain stimulation. *Clin Neurophysiol* 115, 2431-2441.

Lertmanorat Z & Durand D M (2004). Extracellular voltage profile for reversing the recruitment order of peripheral nerve stimulation: a simulation study. *J Neural Eng* 1, 202-211.

Lertmanorat Z & Durand D M (2004). A novel electrode array for diameter-dependent control of axonal excitability: a simulation study. *IEEE Trans Biomed Eng* 51, 1242-1250.

Manola L, Roelofsen B H, Holsheimer J, Marani E & Geelen j (2005). Modelling motor cortex stimulation for chronic pain control: electrical potential field, activating functions and responses of simple nerve fibre models. *Med Biol Eng Comput* 43, 335-343.

Matsuda Y, Yano M, Kitayama M, Kogure S & Yamauchi T (2003). Epileptogenesis induced by alternate-site kindling in bilateral hippocampi. *Epilepsia* 44, 292-298.

Mcintyre C C & Grill W M (1999). Excitation of central nervous system neurons by nonuniform electric fields. *Biophys J* 76, 878-888.

McIntyre C C & Grill W M (2000). Selective microstimulation of central nervous system neurons. *Ann Biomed Eng* 28, 219-233.

McIntyre C C & Grill W M (2001). Finite element analysis of the current-density and electric field generated by metal microelectrodes. *Ann Biomed Eng* 29, 227-235.

McIntyre C C & Grill W M (2002). Extracellular stimulation of central neurons: influence of stimulus waveform and frequency on neuronal output. *J Neurophysiol* 88, 1592-1604.

McIntyre C C, Grill W M, Sherman D L & Thakor N V (2004). Cellular effects of deep brain stimulation: model-based analysis of activation and inhibition. *J Neurophysiol* 91, 1457-1469.

McIntyre C C, Mori S, Sherman D L, Thakor N V & Vitek J L (2004). Electric field and stimulating influence generated by deep brain stimulation of the subthalamic nucleus. *Clin Neurophysiol* 115, 589-595.

Menkes D L & Gruenthal M (2000). Slow-frequency repetitive transcranial magnetic stimulation in a patient with focal cortical dysplasia. *Epilepsia* 41, 240-242.

Mie M, Endoh T, Yanagida Y, Kobatake E & Aizawa M (2003). Induction of neural differentiation by electrically stimulated gene expression of NeuroD2. *J Biotechnol* 100, 231-238.

Miklavcic D, Berays K, Semrov D, Cemazar M, Demsar F & Sersa G (1998). The importance of electric field distribution for effective in vivo electroporation of tissues. *Biophys J* 74, 2152-2158.

Miklavcic D, Pucihar G, Pavlovec M, Ribaric S, *Mali* M, Macek-Lebar A, Petkovsek M, Nastran J, Kranjc S, Cemazar M & Sersa G (2005). The effect of high frequency electric pulses on muscle contractions and antitumor efficiency in vivo for a potential use in clinical electrochemotherapy. *Bioelectrochemistry* 65, 121-128.

Misawa S, Kuwabara S, Shibuya K, Mamada K & Hattori T (2005). Low-frequency transcranial magnetic stimulation for epilepsia partialis continua due to cortical dysplasia. *Neurol Sci* 234, 37-39.

Miyoshi S, Shimizu S, Matsushima J & Ifukube T (1999). Proposal of a new method for narrowing and moving the stimulated region of cochlear implants: animal experiment and numerical analysis. *IEEE Trans Biomed Eng* 46, 451-460.

Moro E, Esselink R J, Xie J, Hommel M, Benabid A L & Pollak P (2002). The impact on Parkinson's disease of electrical parameter settings in STN stimulation. *Neurology* 59, 706-713.

Mutani R & Fariello R (1969). Effect of low frequency caudate stimulation on the EEG of epileptic neocortex. *Brain Res* 14, 749-753.

Nakagawa M & Durand D (1991). Suppression of spontaneous epileptiform activity with applied currents. *Brain Res* 567, 241-247.

Nakamura S (1975). Two types of inhibitory effects upon brain stem reticular neurons by low frequency stimulation of raphe nucleus in the rat. *Brain Res* 93, 140-144.

Plonsey R & Barr R C (1995). Electric field stimulation of excitable tissue. *IEEE Trans Biomed Eng* 42, 329-336.

Plonsey R & Barr R C (1998). Electric field stimulation of excitable tissue. *IEEE Eng Med Biol Mag* 17, 130-137.

Puc M, Corovic S, Flisar K, Petkovsek M, Nastran J & Miklavcic D (2004). Techniques of signal generation required for electropermeabilization. Survey of electropermeabilization devices. *Bioelectrochemistry* 64, 113-124.

Pucihar G, Mir L M & Miklavcic D (2002). The effect of pulse repetition frequency on the uptake into electropermeabilized cells in vitro with possible applications in electrochemotherapy. *Bioelectrochemistry* 57, 167-172.

Pumir A, Plaza F & Krinsky V I (1994). Effect of an externally applied electric field on excitation propagation in the cardiac muscle. *Chaos* 4, 547-555.

Rattay F & Resatz S (2004). Effective electrode configuration for selective stimulation with inner eye prostheses. *IEEE Trans Biomed Eng* 51, 1659-1664.

Rossi S, Ulivelli M, Bartalini S, Galli R, Passero S, Battistini N & Vatti G (2004). Reduction of cortical myoclonus-related epileptic activity following slow-frequency rTMS. *Neuroreport* 15, 293-296

Santos-Anderson R M & Routtenberg A (1976). Stimulation of rat medial or sulcal prefrontal cortex during passive avoidance learning selectively influences retention performance. *Brain Res* 103, 243-259.

Satkauskas S, Andre F, Bureau M F, Scherman D, Miklavcic D & Mir L M (2005). Electrophoretic Component of Electric Pulses Determines the Efficacy of In Vivo DNA Electrotransfer. *Hum Gene Ther.*

Sepulveda N G, Walker C F & Heath R G (1983). Finite element analysis of current pathways with implanted electrodes. *J Biomed Eng* 5, 41-48.

Skelton R W, Miller J J & Phillips A G (1983). Low-frequency stimulation of the perforant path produces long-term potentiation in the dentate gyrus of unanesthetized rats. *Can J Physiol Pharmacol* 61, 1156-1161.

Struijk J J & Holsheimer J (1996). Transverse tripolar spinal cord stimulation: theoretical performance of a dual channel system. *Med Biol Eng Comput* 34, 273-279.

Struijk J J, Holsheimer J, Spincemaille G H, Gielen F L & Hoekema R (1998). Theoretical performance and clinical evaluation of transverse tripolar spinal cord stimulation. *IEEE Trans Rehabil Eng* 6, 277-285.

Susil R C, Sobie E A & Tung L (1999). Separation between virtual sources modifies the response of cardiac tissue to field stimulation. *J Cardiovasc Electrophysiol* 10, 715-727.

Tai C, de Groat W C, Roppolo J R. Simulation of nerve block by high-frequency sinusoidal electrical current based on the Hodgkin-Huxley model. IEEE Trans Neural Syst Rehabil Eng. 2005 September; 13(3):415-22.

Tergau F, Naumann U, Paulus W & Steinhoff B J (1999). Low-frequency repetitive transcranial magnetic stimulation improves intractable epilepsy. *Lancet* 353, 2209.

Ueno S T, T; Harada. k (1988). Localized stimulation of neural tissues in the brain by means of paried configuration of time-varying magnetic fields. *Journal of Applied Phys.* 64, 5862-5864.

Velisek L, Dreier J P, Stanton P K, Heinemann U & Moshe S L (1994). Lowering of extracellular pH suppresses low-Mg(2+)-induces seizures in combined entorhinal cortex-hippocampal slices. *Exp Brain Res* 101, 44-52.

Velisek L, Veliskova J & Stanton P K (2002). Low-frequency stimulation of the kindling focus delays basolateral amygdala kindling in immature rats. *Neurosci Lett* 326, 61-63.

Weiss S R, Li X L, Rosen J B, Li H, Heynen T & Post R M (1995). Quenching: inhibition of development and expression of amygdala kindled seizures with low frequency stimulation. *Neuroreport* 6, 2171-2176.

Wieraszko A (2004). Amplification of evoked potentials recorded from mouse hippocampal slices by very low repetition rate pulsed magnetic fields. *Bioelectromagnetics* 25, 537-544.

Windels F, Bruet N, Poupard A, Feuerstein C, Bertrand A & Savasta M (2003). Influence of the frequency parameter on extracellular glutamate and gamma-aminobutyric acid in substantia nigra and globus pallidus during electrical stimulation of subthalamic nucleus in rats. *J Neurosci Res* 72, 259-267.

Yamamoto T, Katayama Y, Fukaya C, Oshima H, Kasai M & Kobayashi K (2001). New method of deep brain stimulation therapy with two electrodes implanted in parallel and side by side. *J Neurosurg* 95, 1075-1078.

What is claimed is:

1. A method for configuring a stimulation signal applied to a target tissue, comprising:
    establishing an implantable neurostimulator for creating a base stimulation signal, said stimulation signal having at least a first series of first pulses;
    providing a processor within said neurostimulator;
    deconstructing said at least first series of pulses by said processor into at least a first and a second partial pulse series having a plurality of first and second partial electrical pulses respectively which in summation are substantially equal to said base stimulation signal, wherein the second partial electrical pulses of the second partial pulse series are applied with said first partial electrical pulses in at least a partially overlapping manner during at least a portion of a selected time interval; and,
    operating at least one programmable signal generator to provide a constant amplitude of combined stimulation pulses by applying the at least first and second partial pulse series to a plurality of contacts of at least one electrode positioned to stimulate said target tissue.

2. The method of claim 1 wherein during a time within said time interval that said second partial electrical pulses overlap said first partial electrical pulses the first partial electrical pulses are simultaneously applied with the second partial electrical pulses.

3. The method of claim 1 wherein the first partial pulse series and said second partial pulse series have pulses that are subthreshold, but form a stimulus that is above threshold and able to modulate neural targets that are in areas where the electrical fields of the first and second partial electrical pulses spatially overlap.

4. The method of claim 1 wherein, the plurality of pulses of the first and second partial pulse series form an interleaved series of pulses across an interval.

5. The method of claim 1 wherein, the pulses are at least one selected from the group of: unipolar pulses and bipolar pulses.

6. The method of claim 1 wherein, a spectral profile of the first and second partial electrical pulses contains higher frequencies than a spectral profile of the base stimulation signal.

7. The method of claim 1 wherein, the first partial pulse series signal is created by subtracting the second partial pulse signal from the base stimulation signal.

8. The method of claim 1, wherein operating the processor of the device deconstructs at least the first series of pulses into at least a first and a second partial pulse series and at least a portion of each pulse of the first series of pulses forms a series of pulses of at least the first and second partial pulse series.

9. The method of claim 1, wherein operating the processor of the device deconstructs at least the first series of pulses into at least a first and a second partial pulse series and at least a portion of each pulse of the first series of pulses is fractionated into pulses of at least the first and second partial pulse series.

10. The method of claim 1, wherein operating the processor of the device deconstructs at least the first series of pulses into at least a first and a second partial pulse series and at least a portion of each pulse of the first series of pulses is fractionated into pulses of at least the first partial pulse series.

11. The method of claim 1 wherein, the first partial pulse series and second partial pulse series are applied to at least a pair of secondary contacts if determination is made that therapeutic benefit is not obtained during a therapy session.

12. The method of claim 1, further including sensing electroencephalogram (EEG) data related to a disorder and adjusting the stimulation signal based upon evaluation of said EEG sensed data.

13. The method of claim 1, wherein the electrical stimulation is provided for the treatment of a movement disorder.

14. The method of claim 1, wherein the stimulation signal applied to said target tissue provides electrical stimulation for the treatment of a psychiatric disorder.

15. The method of claim 1, wherein the first and second partial electrical pulses each have repetition rate above 4 kHz.

16. The method of claim 1, wherein the combined electrical energy of the first and second partial electrical pulses provide a constant current stimulation.

17. The method of claim 1, wherein contacts of at least one electrode leader are adapted to be positioned in a patient's brain for providing a combined vector summation stimulation resulting from said first and second partial electrical pulses.

* * * * *